(12) United States Patent
Matsumoto et al.

(10) Patent No.: US 7,035,738 B2
(45) Date of Patent: Apr. 25, 2006

(54) PROBE DESIGNING APPARATUS AND PROBE DESIGNING METHOD

(75) Inventors: Toshiko Matsumoto, Kanagawa (JP);
Ryo Nakashige, Kanagawa (JP);
Yasuyuki Nozaki, Kanagawa (JP);
Shingo Ueno, Kanagawa (JP); Takuro Tamura, Kanagawa (JP)

(73) Assignee: Hitachi Sofware Engineering Co., Ltd., Kanagawa (JP)

( * ) Notice: Subject to any disclaimer, the term of this patent is extended or adjusted under 35 U.S.C. 154(b) by 198 days.

(21) Appl. No.: 10/141,099

(22) Filed: May 7, 2002

(65) Prior Publication Data
US 2003/0069701 A1 Apr. 10, 2003

(30) Foreign Application Priority Data
May 29, 2001 (JP) .............................. 2001-161034

(51) Int. Cl.
*G01N 33/48* (2006.01)
*G06G 7/48* (2006.01)
*C12Q 1/68* (2006.01)

(52) U.S. Cl. ........................... 702/19; 702/20; 703/11; 435/6; 536/23.1

(58) Field of Classification Search .................. 702/19, 702/20; 435/6; 536/23.1, 24.5; 707/102
See application file for complete search history.

(56) References Cited

U.S. PATENT DOCUMENTS

| 5,556,749 | A  | * | 9/1996  | Mitsuhashi et al. | ............ | 435/6   |
|-----------|----|---|---------|-------------------|--------------|---------|
| 5,861,242 | A  | * | 1/1999  | Chee et al.       | ............ | 435/5   |
| 6,228,575 | B1 | * | 5/2001  | Gingeras et al.   | ............ | 435/5   |
| 2002/0158906 | A1 | * | 10/2002 | Hashida et al. | ............ | 345/763 |
| 2002/0160401 | A1 | * | 10/2002 | Nozaki et al.  | ............ | 435/6   |
| 2003/0120432 | A1 | * | 6/2003  | Zhou et al.    | ............ | 702/20  |
| 2003/0236633 | A1 | * | 12/2003 | Mei et al.     | ............ | 702/20  |

OTHER PUBLICATIONS

Lathe, R. J. Mol. Bio. (1985) vol. 183, pp. 1-12.*
Behr et al. System. Appl. Microbiol. (Dec. 2000) vol. 23, pp. 563-572.*
Kurata et al., "Probe Design for DNA Chips", 1999 Genome Informancs pp 225-226.
Example 1: Influenza is likely to contribute to a complication with bacterial pneumonia (Kakogawa-shi, Kako-gun, Medical, pp. 1-2, http://www.kakogawa.or.ip/kakomed/memo20.3htm, 1998.
Example 2: MRSA (methicillia resistant *staphlococcus aureus*) simultaneously exists with *Pseudomonas aeruginosa* with high probability (Homepage of Inasa Redcross Hospital, updated Jul. 26, 1996, pp. 1-4, http://www.habi.ne.jp/rc-inasa/topics.html.

* cited by examiner

*Primary Examiner*—Mary K. Zeman
(74) *Attorney, Agent, or Firm*—Reed Smith LLP; Stanley P. Fisher, Esq.; Juan Carlos A. Marquez, Esq.

(57) ABSTRACT

Where a DNA chip corresponding to a bacterium that is a subsequently added identification object is produced, temporal and pecuniary cost is reduced, and even where a probe unique to the DNA sequence of an identification object cannot be designed, precision in identifying DNA comprised in a sample is maximized. First, on designing a probe, a plurality of different probes are prepared to one kind of bacterium. Where some probes come to be not available by addition of bacteria that are new identification objects, identification is carried out using the remaining probes. Where a probe unique to an identification target bacterium cannot be designed, a probability of correct identification is increased by using multiple probes. Moreover, in consideration with a possibility that multiple kinds of bacteria simultaneously exist, a combination of probes that maximizes a probability of correct identification is selected.

4 Claims, 25 Drawing Sheets

FIG. 5

| Chip identification name : M001218 | | | Designed: Dec. 18, 2000 | | Latest update: Feb. 21, 2001 | |
|---|---|---|---|---|---|---|
| Number of object bacteria: 35 | | | | | | |
| No | Name of bacteria | Number of probes | No | Sequence | Location | Reaction temperature | ... |
| 1 | E coli | 8 | 1 | T T A A G T A G A ... | From 182nd base | 55°C | |
| 2 | Staphylococcus aureus | 11 | 2 | G T T A A G T A G ... | From 251st base | 53°C | |
| 3 | Salmonella | 12 | 3 | T T G G G A G T A ... | From 61st base | 53°C | |
| 4 | Salmonella typhi | 7 | 4 | G C T T G G G G A ... | From 138th base | 55°C | |
| ⋮ | | | ⋮ | | ⋮ | | |
| 35 | | | 11 | | | | |

FIG. 6

Bacteria Data

| | Name of members | Value |
|---|---|---|
| 600 | Bacterium ID | 1 |
| 601 | Common name | Typhus-kin |
| 602 | Scientific name | Salmonella typhi |
| 603 | DNA sequence | G T T A A T A C C ··· |
| 604 | Detection site | Blood, marrow humor, stool, urine, bile |
| 605 | Bacteria causing complication and mixed infection | (1 and 3),(1,15 and 24) |

FIG. 10

```
DNA sequence P    TCGAATGACGAAGGGTTCTGATCCTGTACCC
DNA sequence Q    TCTGATCCATTCGGGTTCTTCTACCATTAGG
DNA sequence R    ATAGACCACGAGGACTCGCTGTACCATTCGG
```

⬇ Step 900
List partial sequences

```
DNA sequence P    TCGAATGACGAAGGGTTCTGATCCTGTACCC
                  TCGAATG
                   CGAATGA
                    GAATGAC
                     AATGACG
                      ATGACGA
                       TGACGAA
                         ⋱
```

```
DNA sequence Q    TCTGATCCATTCGGGTTCTTCTACCATTAGG
                  TCTGATC
                   CTGATCC
                    TGATCCA
                     GATCCAT
                      ATCCATT
                         ⋱
```

```
DNA sequence R    ATAGACCACGAGGACTCGCTGTACCATTCGG
                  ATAGACC
                   TAGACCA
                    AGACCAC
                     GACCACG
                        ⋱
```

⬇ Steps 901 to 903
Select probe candidates with conditions of Tm value, degree of intertwining with itself, degree of mishybridization, etc.

```
DNA sequence P    TCGAATGACGAAGGGTTCTGATCCTGTACCC
                   CGAATGA     GAAGGGT       TCCTGTA
                              AAGGGTT
```

```
DNA sequence Q    TCTGATCCATTCGGGTTCTTCTACCATTAGG
                  TCTGATC                   ACCATTA
                  TGATCCA
```

```
DNA sequence R    ATAGACCACGAGGACTCGCTGTACCATTCGG
                       CCACGAG       TCGCTGT
                        ACGAGGA
```

⬇ Step 904
Select a unique probe candidate. Where no unique candidates exist, multiple probes are used for substitution.

FIG. 11

Probe candidate 1 of bacterium P
GC content = 2
Probe candidate 2 of bacterium P
GC content = 1
Probe candidate 3 of bacterium P
GC content = 3

DNA of bacterium P ··T C G A A T A A C G A A G A C T T T C A T T C A T T A C G C A T ···
DNA of bacterium Q ··T C G A G G T A C A A A G T G C T A C C A T T A G G T C G A C A T ···

GC content = 3
Probe candidate 1 of bacterium Q
Probe candidate 2 of bacterium Q
GC content = 4

FIG. 19

DNA of bacterium P　　　・・・TCGAATGA<u>CGAAGACT</u>TCTGATCCATTCGGCCATTACCTACAT・・・
DNA of bacterium Q　　　・・・TCGAATGATATCGTATCTGATCG<u>GCTATACAG</u>CCCTACAT・・・
DNA of bacterium Y　　　・・・TCGAATGATCTATCGTATA<u>AACTAATAT</u>ACGGATTACCTACAT・・・

↑　　↑
　　　　　　　　　　　　　　Probe of bacterium P　Probe of bacterium Q
　　　　　　　　　　　　　　　　　Probe of bacterium Y DNA of bacterium X　　　・・・TCAGTTCAATGATCGTATA<u>ACTACTAT</u>ACGGCATTACCTACAT・・・
that is subsequently
added to identification objects Portion having high possibility of mishybridizing
　　　　　　　　　　　　　　　　with probe of bacterium Y

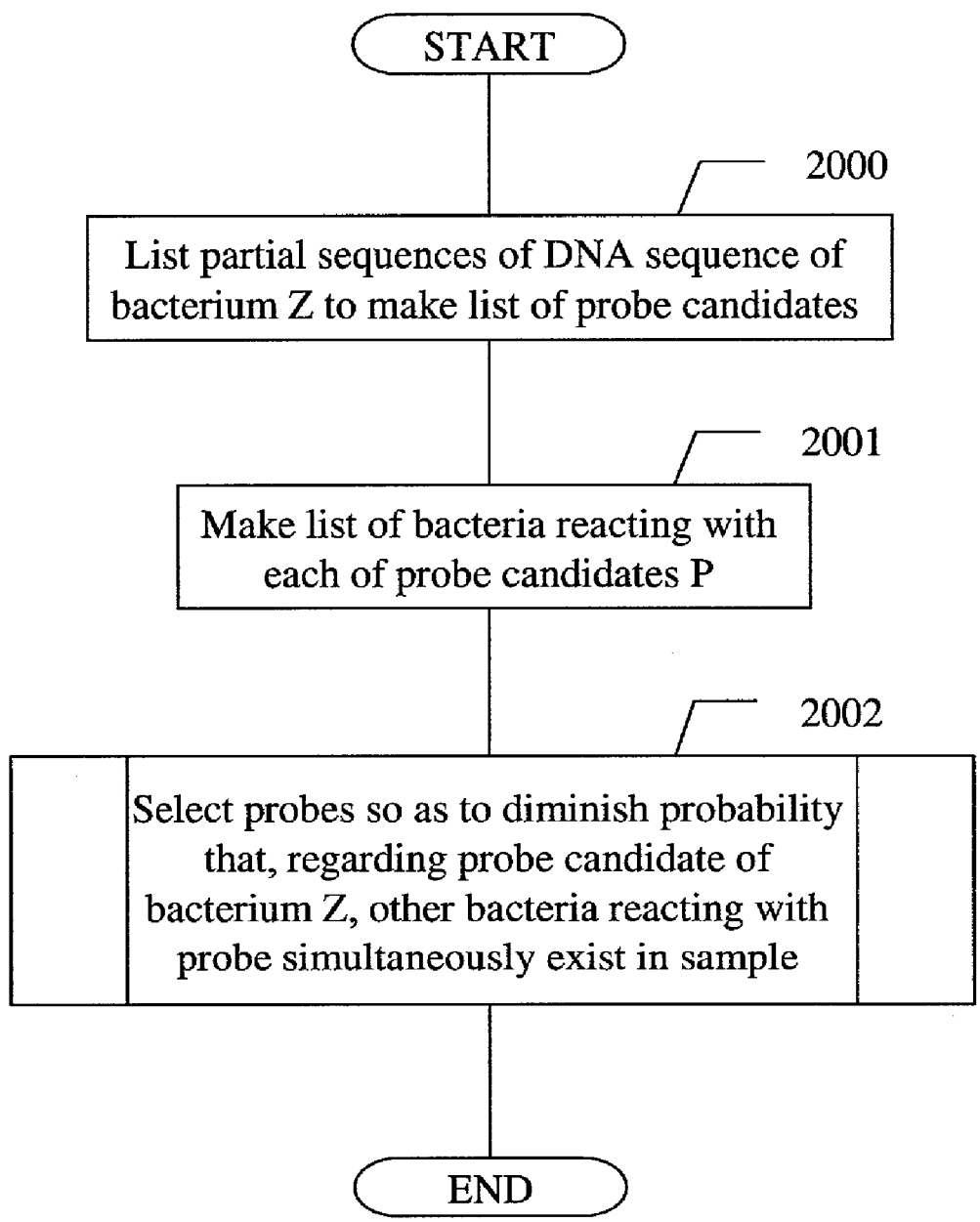

FIG. 22

Case of using probe candidate P1 as probe for bacterium Z

| Presence of bacteria | | Probe signal | |
|---|---|---|---|
| Bacterium B1 | Bacterium Z | Probe of bacterium B1 | Probe candidate P1 |
| ○ | ○ | ○ | ○ |
| × | ○ | × | ○ |
| ○ | × | ○ | ○ |
| × | × | × | × |

Impossible to determine whether or not the Bacterium Z exists

Case of using probe candidates P1 and P2 as probes for bacterium Z

| Presence of bacteria | | | Probe signal | |
|---|---|---|---|---|
| Bacterium B1 | Bacterium B2 | Bacterium Z | Probe candidate P1 | Probe candidate P2 |
| ○ | ○ | ○ | ○ | ○ |
| × | ○ | ○ | ○ | ○ |
| ○ | × | ○ | ○ | ○ |
| × | × | ○ | ○ | ○ |
| ○ | ○ | × | ○ | ○ |
| × | ○ | × | × | ○ |
| ○ | × | × | ○ | × |
| × | × | × | × | × |

Bacterium Z does not exist, but signal exists

| Probe candidates to be used | Case where the presence of the bacterium Z cannot be determined |
|---|---|
| Probe candidates P1 and P2 | Both bacterium B1 and bacterium B2 exist |
| Probe candidates P2 and P3 | Bacterium B2 exists, and bacterium B3 or B4 also exists |
| Probe candidates P1 and P3 | Bacterium B1 exists, and bacterium B3 or B4 also exists |

FIG. 24

| | | | 2402 | 2400 | 2403 | 2404 | 2406 | 2405 2401 | |
|---|---|---|---|---|---|---|---|---|---|

| No | Selected | Bacteria name (Common name) | Bacteria name (Scientific name) | Detection site | |
|---|---|---|---|---|---|
| 1 | | Daicho-kin | Escherichia coli | Blood, marrow humor, stool, urine, bile | ▲ |
| 2 | ▼ | Oshokubudokyu-kin | Staphylococcus aureus | Blood, marrow humor, mucus, stool, pus | |
| 3 | | Salmonella-kin | Salmonella | Stool, blood, puncture fluid, lymph | |
| 4 | | Typhus-kin | Salmonella Typhi | Blood, marrow humor, stool, urine, bile | |
| 5 | ▼ | Cholera-kin | Vibrio cholerae | Stool | |
| 6 | | Pest-kin | Yersinia pestis | Blood, sputum | |
| 7 | ▼ | Sekiri-kin | Shigella dysenteriae | Stool | ▽ |

Chip identification name / M001218 / Number of selected bacteria : 12

Determination — 2407

FIG. 25

| No | Selected | Bacteria name (Common name) | Bacteria name (Scientific name) | Detection site |
|---|---|---|---|---|
| 1 |  | Daicho-kin | Escherichia coli | Blood, marrow humor, stool, urine, bile |
| 2 | ▼ | Oshokubudokyu-kin | Staphylococcus aureus | Blood, marrow humor, mucus, stool, pus |
| 3 | ▼ | Salmonella-kin | Salmonella | Stool, blood, puncture fluid, lymph |
| 4 |  | Typhus-kin | Salmonella Typhi | Blood, marrow humor, stool, urine, bile |
| 5 | ▼ | Cholera-kin | Vibrio cholerae | Stool |
| 6 |  | Pest-kin | Yersinia pestis | Blood, sputum |
| 7 | ▼ | Sekiri-kin | Shigella dysenteriae | Stool |

Chip identification name: M001218
Designing date: DEC. 8, 2000
Latest update: Apr. 11, 2001
Number of selected bacteria: 12
Number of bacteria added: 3

Cancellation   Determination

PROBE DESIGNING APPARATUS AND PROBE DESIGNING METHOD

FIELD OF THE INVENTION

The present invention relates to a DNA chip technique for identifying multiple kinds of DNA contained in a target.

BACKGROUND OF THE INVENTION

With developments in gene-analysis techniques in recent years, functions and structures of genes have gradually been clarified. In particular, a technique regarding a DNA chip or a DNA microarray (hereinafter referred to collectively as a DNA chip) is a focus of attention as an effective means for gene analysis.

A DNA chip comprises a large number of different DNA molecules (probes) located at a high density on the surface of a substrate such as glass, silicon or plastic. As a probe, a cDNA (PCR fragment), or a short chain nucleotide of about 20 to 30 mer, or the like is typically used. The principle of DNA chip is based on hybridization, or the property of 4 bases, A (adenine), T (thymine), G (guanine) and C (cytosine), whereby a hydrogen bond occurs between A and T, and G and C. A DNA or RNA (a target) labeled with a fluorescent substance or the like is captured when it hybridizes with a probe on the DNA chip. The captured DNA is detected as a fluorescent signal from each spot, and by data analysis of the signal with a computer, several thousands to several tens of thousands of DNA molecules in a sample can be observed at once.

One of methods of using DNA chip is a method (SBH method) for observing whether DNA to be examined is contained in a sample by capturing a gene (or a DNA fragment) in the sample, reading the sequence of the captured DNA, or examining the polymorphic portion of DNA such as SNP or the like.

As an example of the methods of using DNA chip, identification of bacteria in a clinical test will be explained. Since it has previously been necessary to culture a bacterium to observe the form or biochemical properties thereof or to confirm the immune response, in order to identify the bacterium in a clinical test, the test has required many days. Moreover, to identify multiple kinds of bacteria, it has been necessary to separately perform a biological experiment for each kind of bacterium. Accordingly, on an actual clinical site, in terms of time or cost, identification of bacteria is performed, targeting only bacteria with a high separation frequency, and so there is a problem of poor precision in identifying bacteria, which have a low separation frequency and develop a serious symptom.

In identification of bacteria by using a DNA chip, the DNA sequence information of each bacterium is obtained from DNA sequence database and so on. For each bacterium, a specific partial sequence is selected from the DNA sequence and located on a DNA chip as a probe. On the other hand, the DNA of a bacterium is extracted from a sample such as blood or sputum collected from a patient, and after amplification by PCR, it is reacted with the DNA chip.

FIG. 1 is a figure schematically showing this identification. In respect of 20 kinds of bacteria such as a bacterium P (SEQ ID NO. 1), Q (SEQ ID NO. 2) or R (SEQ ID NO. 3), a specific partial sequence is independently selected from each DNA sequence and located on a DNA chip. The positions of these probes are represented by horizontal Nos. 1 to 5 and vertical Nos. 1 to 4. It is assumed that, as a result of reaction of a sample 110 containing the DNA of a bacterium extracted from blood or sputum collected from a patient, with a probe on a DNA chip 100, signals are observed from two spots corresponding to (horizontal No. 1, vertical No. 2) and (horizontal No. 3 and vertical No. 5). Then, referring to a table controlling information on probe position, it is found that a bacterium (horizontal No. 1, vertical No. 2) and a bacterium (horizontal No. 3, vertical No. 5) are mixed into the sample.

Thus, in identification of bacteria with a DNA chip, since multiple kinds of probes can be located on the chip, many kinds of bacteria can exhaustively be detected with a single chip. Moreover, since there is no need for culturing bacteria, time required for detection can be reduced.

Identification of bacteria with a DNA chip is expected to be available in a hospital, a public health center, a quarantine station, etc. in the future. These institutions do not need to design a probe to be located on a DNA chip or to prepare a probe or DNA chip preparation device, and can make detection using a chip purchased, and so the institutions can simply use this identification of bacteria with a DNA chip.

There are two problems to use the above described DNA chip on an actual site. The first problem is that much time and efforts are required to produce a DNA chip that is ready for a new bacterium, where an identification object DNA is newly added after probes located on a DNA chip are designed. For example, in actual identification of bacteria in a clinical test or food evaluation, as example cases stated below, bacteria that have not been a focus of attention or a new type of bacteria that have appeared by mutation, prevail, and there may be a need for detection and identification of them.

Case 1: There appeared by mutation, *Staphylococcus aureus* or *Pseudomonas aeruginosa* that acquired drug resistance.

Case 2: Due to prevalence of food poisoning, demand for detection of bacteria that caused the poisoning is rapidly increased.

These new bacteria cannot be detected or identified with probes that have previously been used. Consequently, to cope with a newly added bacterium, there is a need to revise information of probes spotted on a DNA chip and to make detection, using a DNA chip produced on a basis of new probe information.

However, when an identification object bacterium is newly added, probes ready for the existing bacteria should also be altered. The currently proposed method for designing a probe for a DNA chip comprises, first, listing partial sequences unique to each of DNA sequences as probe candidates; considering conditions such as:

to ensure a uniform reaction temperature on each spot,
to ensure that a probe does not intertwine with itself, and
to reduce a probability of mishybridization; and narrowing the candidates so as to obtain an optimum combination of probes (Kenichi Kurata et al.: Probe Design for DNA Chips: *Genome Informatics*, 1999, pp. 225–6, 1999). However, when a new identification object bacterium is added, the probe loses uniqueness, the reaction temperature becomes ununiform, or the probability of mishybridization increases, and accordingly there is a fear that many probes come to be not optimum.

FIG. 2 shows a state in which probes come to be not optimum by addition of a new identification object bacterium. Ellipses enclosed with solid lines represent processes of selecting probes on newly designing a DNA chip, that is, before addition of an identification object bacterium. The ellipses each represent, a whole partial sequence 200; a unique partial sequence group 211 that is unique when designing a DNA chip; a probe candidate group 212 that is unique and has a uniform reaction temperature when designing the chip; a probe candidate group 213 that is unique, has a uniform reaction temperature and does not intertwine with itself when designing the chip; a probe candidate group 214 that is unique, has a uniform reaction temperature, does not intertwine with itself and has a low probability of mishybridization. Probe candidates 221, 222 and 223 that are shown in the figure, are examples that are eliminated from candidates for the reasons that it does not meet the reaction temperature condition, it intertwines with itself and it has a high probability of mishybridization, respectively. Thus, probe candidates are narrowed by strengthening conditions, and probes 231 and 232 contained in the group 214 located the most inside are used.

Then, it is assumed that groups which meet each of the conditions shift from ones with solid lines to ones with dotted lines. That is to say, a group 241 shown in a dotted line represents a group of partial sequences that are unique when a bacterium is added; a group 242 represents a group of probe candidates that are unique and have a uniform reaction temperature when the bacterium is added; a group 243 represents a group of probe candidates that are unique, have a uniform reaction temperature and do not intertwine with themselves when the bacterium is added; a group 244 represents a group of probe candidates that are unique, have a uniform reaction temperature, do not intertwine with themselves and have a low probability of mishybridization when the bacterium is added. As a result, the probe 231 has a high probability of mishybridization and the probe 232 loses uniqueness, and so these two probes come to be not optimum by new addition of a bacterium.

To cope with a newly added identification object bacterium, where an optimum combination of probes is newly selected against input including a new bacterium, applying the above described algorithm, many probes such as the probes 231 and 232 shown in FIG. 2 should be substituted.

To produce a DNA chip ready for a new bacterium, DNA chip manufacturing companies need to confirm effectiveness of every newly added probe by a verification experiment and to prepare a DNA fragment for a new probe, and so much time and cost are required. Moreover, in a hospital, a public health center, a quarantine station, etc., where detection of bacteria is performed using a DNA chip, it is required to purchase a DNA chip ready for a new bacterium for detection of bacteria, instead of the previous DNA chip to detect bacteria. Especially on actual sites where immediacy is required, it is a large problem that it takes a long time until a new DNA chip is purchased.

The second problem is that it is not necessarily possible to select a probe unique to each identification object DNA. That "a probe is unique" means that a probe is comprised in a DNA sequence as a partial sequence, but it is not comprised in other DNA sequences as a partial sequence. When a unique probe is used, regardless of the presence or absence of other DNAs, a evaluation that "if a signal is observed from this probe, this DNA is mixed, but if it is not observed, the DNA is not mixed" can be made. If a unique partial sequence is prepared as a probe for each kind of DNA, all DNA combinations can properly be determined.

Nevertheless, in some cases, one of identification object DNAs is extremely similar to another DNA, and so a unique partial sequence cannot be selected. FIG. 3 shows an example that a DNA sequence R (SEQ ID NO. 6) does not have the unique partial sequence. Since the DNA sequence R has communality with DNA sequences P (SEQ ID NO. 4) and Q (SEQ ID NO. 5), the unique partial sequence cannot be selected. Since it is assumed in the above probe designing method that a unique partial sequence exist to each of DNA sequences, the method cannot be provided for such a case.

SUMMARY OF THE INVENTION

In view of the above problems with prior art, it is an object of the present invention to provide a probe designing method which flexibly copes with addition of other types of identification object DNA. Moreover, it is another object of the present invention to provide a probe designing method which maximizes precision in identifying DNA comprised in a sample, even where a probe unique to an identification object DNA sequence cannot be designed.

Where a probe unique to identification object DNA cannot be selected, identification is carried out by the following schemes:

A probability of correct identification is increased by using a plurality of probes.

Considering a possibility that multiple kinds of DNA exist simultaneously, a combination of probes that maximizes a probability of correct identification is selected.

According to the schemes, precision in identifying DNA can be improved.

Where an identification object DNA is added subsequently, a DNA chip ready for a new DNA is produced by the following schemes.

When a probe is initially designed, a plurality of different probes are prepared to one kind of DNA. Even where a part of probes comes to be not available by addition of a new identification object DNA, identification can be carried out, using the remaining probes.

Where identification cannot be carried out with the existing probes, a probe is not added if identification can be carried out with medical or biological knowledge. By this, to produce a DNA chip ready for a new bacterium, it is only required to add probes for a portion of DNA, and so temporal and pecuniary cost for performing verification experiments or preparing a DNA fragment for a probe is reduced.

The probe designing apparatus and the probe designing method of the present invention have the following features:

(1) A probe designing apparatus, which designs a probe set for identifying multiple kinds of targets that are identification objects by the medium of hybridization, the probe designing apparatus comprising, an identification object target registration processing unit for registering the information of an identification target comprising a base sequence;

a probe selection processing unit for selecting, as a probe, a partial sequence unique to each of the registered targets, from partial sequences of the base sequence; and a multiple probes substitution processing unit for selecting a combination of multiple probes as a substituted probe to the target, in a case where, in the probe selection processing unit, there remains a target for which a unique partial sequence could not be selected.

(2) A probe designing apparatus, which designs a probe set for identifying multiple kinds of targets that are identification objects by the medium of hybridization, the probe designing apparatus comprising, a means for reading the information of the existing probe set for identifying multiple kinds of targets;

an identification object target addition processing unit for reading information comprising the base sequence of a new target that is to be added to identification objects;

a probe reanalysis processing unit for detecting a target which becomes difficult to be identified by the probes in the existing probe set due to the addition of the new target;

a probe addition processing unit for adding a probe for identifying the new target and a probe for identifying the target detected with the probe reanalysis processing unit;

a multiple probes substitution processing unit for selecting a combination of multiple probes as a substituted probe to the target, in a case where, in the probe addition processing unit, there remains a target for which a unique probe could not be selected; and a probe updation processing unit for updating a probe set by reflecting processing results from the probe addition processing unit and/or the multiple probes substitution processing unit.

(3) The probe designing apparatus according to (1) or (2) above, wherein, in the multiple probes substitution processing unit, by using as a reference, a probability that multiple kinds of targets hybridizing with multiple probes simultaneously exist in a sample, a combination of probes with the low probability is selected as substituted probes.

(4) The probe designing apparatus according to (1) or (2) above, wherein, in the multiple probes substitution processing unit, the probability that multiple kinds of targets hybridizing with multiple probes simultaneously exist in a sample is determined using information regarding a mixed infection and a complication, and a combination of probes with the low probability is selected as substituted probes.

(5) A probe designing method, which designs a probe set for identifying multiple kinds of targets that are identification objects by the medium of hybridization, the probe designing method comprising, a step of reading the data comprising the base sequences of a group of targets that are identification objects;

a step of selecting, as a probe, a partial sequence unique to each target, from partial sequences of the base sequence of each read target; and a step of selecting a combination of multiple probes as substituted probes to the target, in a case where, in the selection step, there remains a target for which a unique partial sequence could not be selected.

(6) A probe designing method, which designs a probe set for identifying multiple kinds of targets that are identification objects by the medium of hybridization, the probe designing method comprising, a step of reading the data of the existing probe set for identifying multiple kinds of targets;

a step of reading the data comprising the base sequence of a new target that is to be added to identification objects;

a step of detecting a target which becomes difficult to be identified by the probe in the existing probe set due to the addition of the new target;

a probe addition step of adding a probe for identifying the new target and a probe for identifying the target which becomes difficult to be identified;

a substituted probe selection step of selecting a combination of multiple probes as a substituted probe to the target, in a case where, in the probe addition step, there remains a target for which a unique probe could not be selected; and a step of updating a probe set by reflecting a probe added in the probe addition step and/or a probe selected in the substituted probe selection step.

(7) The probe designing method according to (5) or (6) above, wherein, in the substituted probe selection step, by using as a reference, a probability that multiple kinds of targets hybridizing with multiple probes simultaneously exist in a sample, a combination of probes with the low probability is selected as substituted probes.

(8) The probe designing method according to (5) or (6) above, wherein, in the substituted probe selection step, the probability that multiple kinds of targets hybridizing with multiple probes simultaneously exist in a sample is determined using information regarding a mixed infection and a complication, and a combination of probes with the low probability is selected as substituted probes.

(9) A program, which allows a computer to execute the probe designing method according to any one of (5) to (8) above.

(10) A computer-readable recording medium, which records a program allowing a computer to execute the probe designing method according to any one of (5) to (8) above.

BRIEF DESCRIPTION OF THE DRAWINGS

FIG. 5 is a figure showing an example of the display screen of a display device.

FIG. 6 is a figure showing the structure of bacteria data.

FIG. 10 is a figure showing shift of a group of probe candidates.

FIG. 11 is a figure showing a process of uniformalizing reaction temperature.

FIG. 19 is a figure showing a state in which a probability of mishybridization is increased by subsequent addition of an identification object bacterium.

FIG. 20 is a figure showing the detailed flow of a processing of substituting by multiple probes, where a probe unique to an identification object bacterium cannot be designed.

FIG. 22 is a figure showing how to select probe candidates and in what case a bacterium cannot be identified.

FIG. 24 is a figure showing an example of the display screen of a display device in a processing of registering an identification object bacterium to a newly designed DNA chip.

FIG. 25 is a figure showing an example of the display screen of a display device in a processing of additively registering an identification object bacterium to the existing DNA chip.

EXPLANATION OF NUMERALS

100: DNA chip, 110: Sample, 400: Bacteria database, 401: DNA chip database, 405: Central Processing Unit, 406: Program memory, 415: Data memory

DESCRIPTION OF THE PREFERRED EMBODIMENTS

Taking identification of bacteria as an example, the embodiments of the present invention will be described below with reference to drawings.

Figure 1:
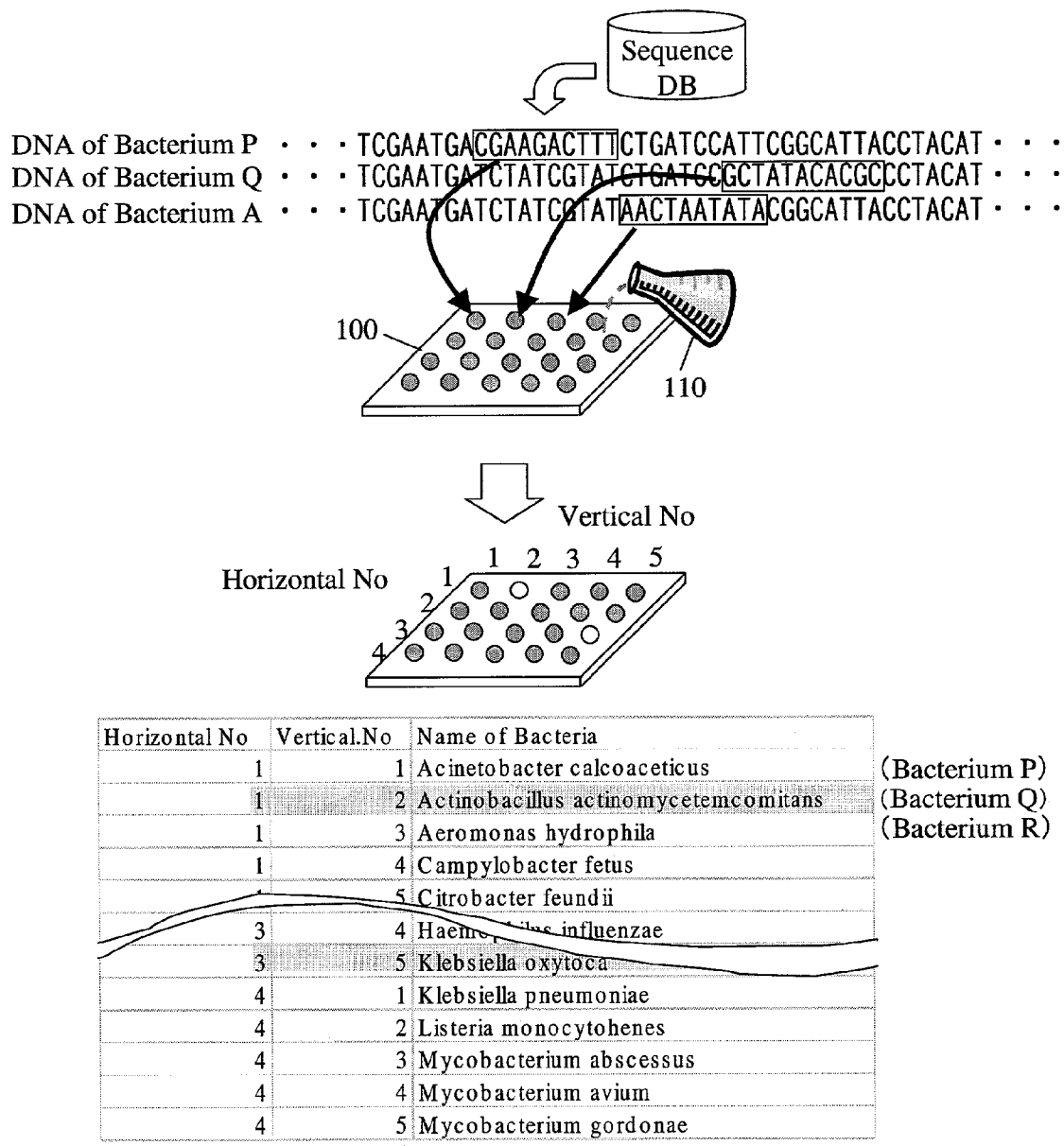
FIG. 1 is a schematic figure of identification of bacteria by using a DNA chip.
Figure 2:
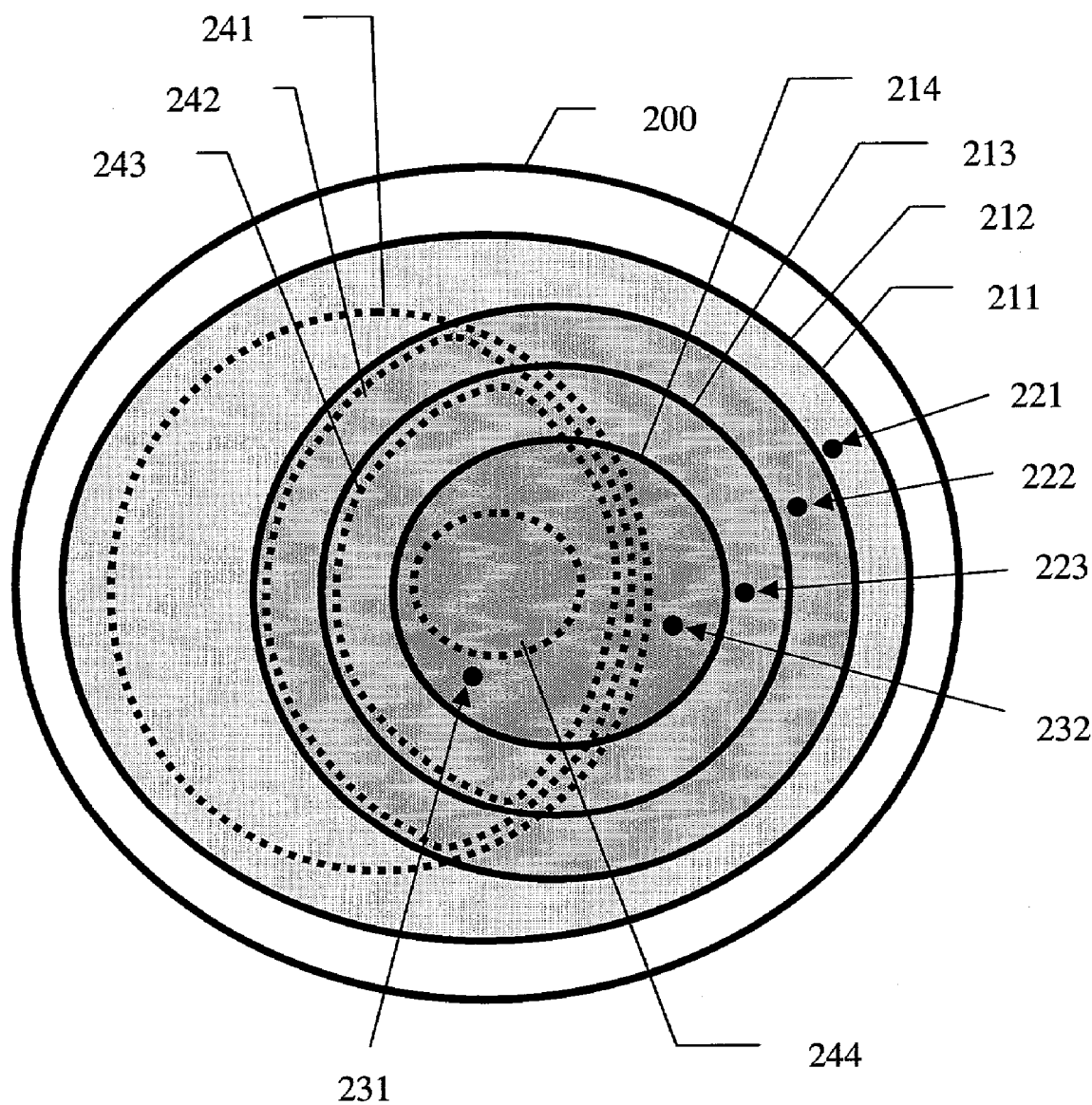
FIG. 2 is a figure showing a process of selecting probes located on a DNA chip.
Figure 3:
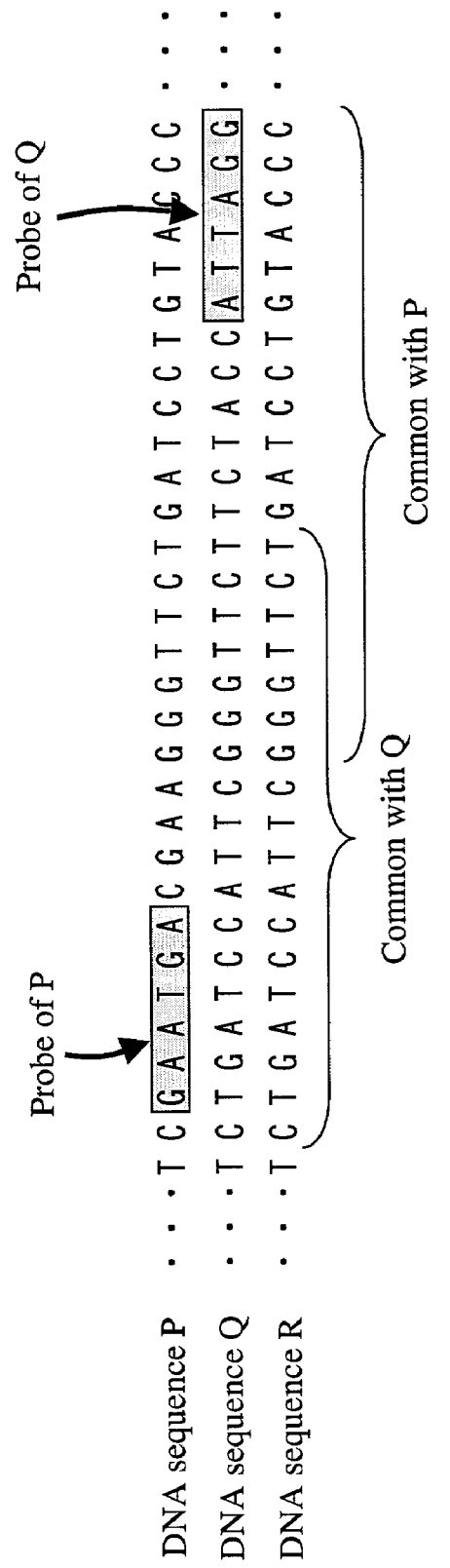
FIG. 3 is a figure showing an example that a probe unique to the DNA of an identification object bacterium cannot be designed.
Figure 4:
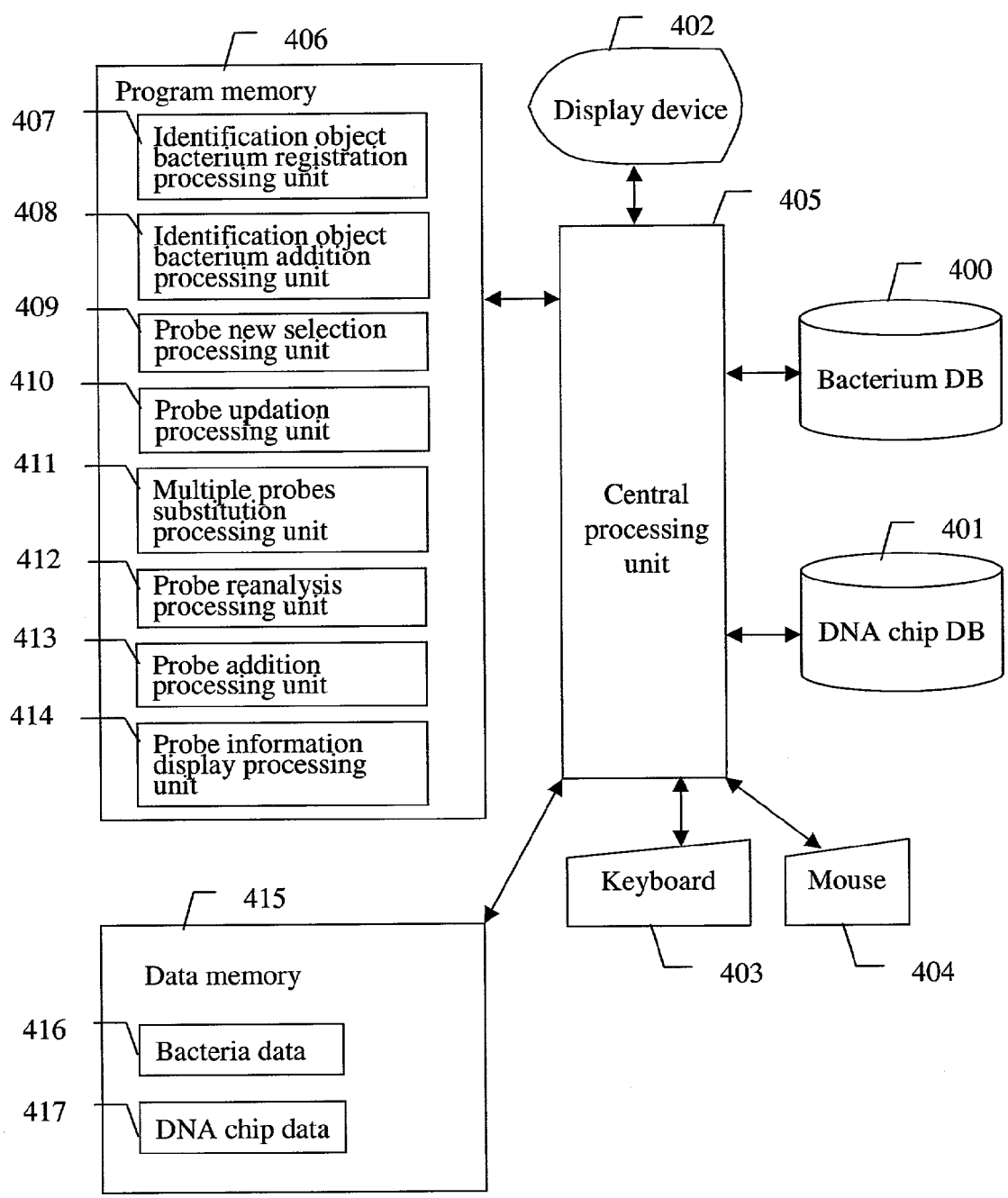
FIG. 4 is a block diagram showing the structure of the DNA chip system of the present invention.

FIG. 4 is a schematic block diagram of the system of the present invention. This system comprises a bacteria database 400 which archives medical and biological information such as information on DNA sequence of bacteria, bacteria detection sites, and a complication or mixed infection, a DNA chip database 401 which archives information on the DNA chip that was already designed (e.g. information on identification object bacteria, probes to each bacterium, etc.), a display device 402 for outputting information on the designed probes, a keyboard 403 and a pointing device 404 such as a mouse for selecting bacteria to be added to identification objects or DNA chip to be updated, a central processing unit 405 for selecting probes, a program memory 406 for storing a program necessary for processes in the central processing unit 405, and a data memory 415 for storing data necessary for processes in the central processing unit 405.

The program memory 406 comprises an identification object bacterium registration processing unit 407 for registering an identification object bacterium when a DNA chip is newly designed, an identification object bacterium addition processing unit 408 for additively registering an identification object bacterium to the existing DNA chip, a probe new selection processing unit 409 for selecting probes when a DNA chip is newly designed, a probe updation processing unit 410 for further selecting probes so that these probes have the experimental conditions matching with the existing probes, when an identification object bacterium is added to the existing DNA chip, and a probe information display processing unit 414 for displaying the designed probe information. Both the probe new selection processing unit 409 and the probe updation processing unit 410 comprise a multiple probes substitution processing unit 411 for substituting by multiple probes, in a case where a probe unique to identification object DNA cannot be designed. The probe updation processing unit 410 comprises a probe reanalysis processing unit 412 which determines whether or not the existing probe can identify the identification object DNA when a bacterium is newly added, and a probe addition processing unit 413 for additively selecting probes so that these probes have the experimental conditions matching with the existing probes.

The data memory 415 comprises bacteria data 416 for retaining data of medical and biological information of bacteria and DNA chip data 417 for retaining data of DNA chip.

FIG. 24 shows an example of a display screen (an identification object bacterium registration screen) by the identification object bacterium registration processing unit 407. This display screen is used for registering an identification object bacterium to design a new DNA chip. 2400 denotes the identification name of the DNA chip. 2401 denotes a list of bacteria that are registered in the bacteria database 400. From this list, an identification object bacterium is selected. 2402 denotes a column for displaying bacteria selected as identification objects. Boxes for the selected bacteria are checkmarked. 2403 denotes the name of bacteria (common name). 2404 denotes the name of bacteria (Scientific name). 2405 denotes sites wherein bacteria are detected. Only the Japanese name, the scientific name and the detection sites of bacteria are displayed herein, but information such as disease condition and DNA sequence data may also be displayed. 2406 denotes the number of the selected bacteria, and the number corresponds to the number of the checkmarks placed in 2402. 2407 denotes a determination button. On pressing this button, a bacterium that is presently selected is determined as an identification object.

FIG. 25 is an example of a display screen (an identification object bacterium addition screen) by the identification object bacterium addition processing unit 408. This display screen is used for adding an identification object bacterium to the existing DNA chip. 2500 denotes the identification name of the DNA chip. 2501 denotes the date of designing the DNA chip. 2502 denotes the date of the latest update of the DNA chip. Both designing date and updating date are herein indicated only by year (A.D.), month and date, but the year may be represented by the Japanese imperial era, or time may also be displayed together with year, month and date. Moreover, information such as update history may also be displayed. 2503 denotes a list of bacteria that are registered in bacteria database, and this is identical to 2401. Bacteria to be added to identification objects are selected herefrom. 2504 denotes a column for displaying bacteria that are added as identification objects. Boxes for the bacteria that are originally identification objects, are fixed while being checkmarked. When a bacterium that is to be newly added to identification objects is selected from bacteria that have not originally been identification objects, checkmarks are newly displayed. 2505 denotes the name of bacteria (common name). 2506 denotes the name of bacteria (Scientific name). 2507 denotes sites wherein bacteria are detected. Herein, only the common name, the scientific name and the detection sites of bacteria are displayed, but information such as disease condition and DNA sequence data may also be displayed. 2508 denotes the number of bacteria that have originally been identification objects, and the number corresponds to the number of the bacteria that are fixed with checkmarks in 2504. 2509 denotes the number of bacteria that are newly added and the number corresponds to the number of checkmarks added to 2504. 2510 is a determination button. On pressing this button, bacteria that are presently selected are added as identification objects. 2511 is a cancellation button. On pressing this button, bacteria that are defined as identification objects, are not changed.

FIG. 5 is an example of a processing screen (a probe selection result display screen) by the probe display processing unit 414. This processing screen is used for displaying information of probes selected by this system. 500 denotes the identification name of the DNA chip. 501 denotes the date of designing the DNA chip. 502 denotes the date of the latest update of the DNA chip. Both designing date and updating date are herein indicated only by year (A.D.), month and date, but the year may be represented by the Japanese imperial era, or time may also be displayed together with year, month and date. Moreover, information such as update history may also be displayed. 503 denotes the number of bacteria that are defined as identification objects by this DNA chip. 504 is a list of bacteria that are defined as identification objects by this DNA chip. The number of lines in this table corresponds to the value in 503. Using the mouse 404 or the keyboard 403, bacteria can be selected from this list. Herein, only the identification number and the common name of bacteria, and the corresponding number of probes are displayed, but information such as the scientific name and the DNA sequence data may also be displayed. 505 denotes a list of probes corresponding to bacteria selected from the list 504. Herein, only the length of probes, the position in the DNA of bacteria, and reaction temperature are displayed, but a probability of intertwining with itself, a probability of mishybridizing with the DNA of other bacteria, and the positional relationship with other probes may also be displayed.

FIG. 6 is an example of a data structure of medical and biological information of bacteria, which is read from the bacteria database 400 and retained in the bacteria data 416 of the data memory 415.

600 denotes the ID number of bacteria. This number is uniquely assigned to all bacteria and so bacteria are distinguished with this number. 601 is the common name. 602 is the scientific name. 603 is the DNA sequence. 604 denotes the sites in which bacterium 1 is detected. 605 denotes a list of the ID number 600 of bacteria that may possibly contribute to a complication or mixed infection with a bacterium ID No. 1. In this figure, it is shown that the bacterium ID No. 1 has a possibility of a mixed infection with a bacterium ID No. 3 and another possibility of a mixed infection with bacteria ID Nos. 15 and 24. 605 is described redundantly. That is, each 605 of bacteria ID Nos. 3, 15 and 24 includes (1 and 3), (1, 15 and 24) and (1, 15 and 24), respectively. In addition to these, information such as species, group and symptoms may be retained.

Figure 7:
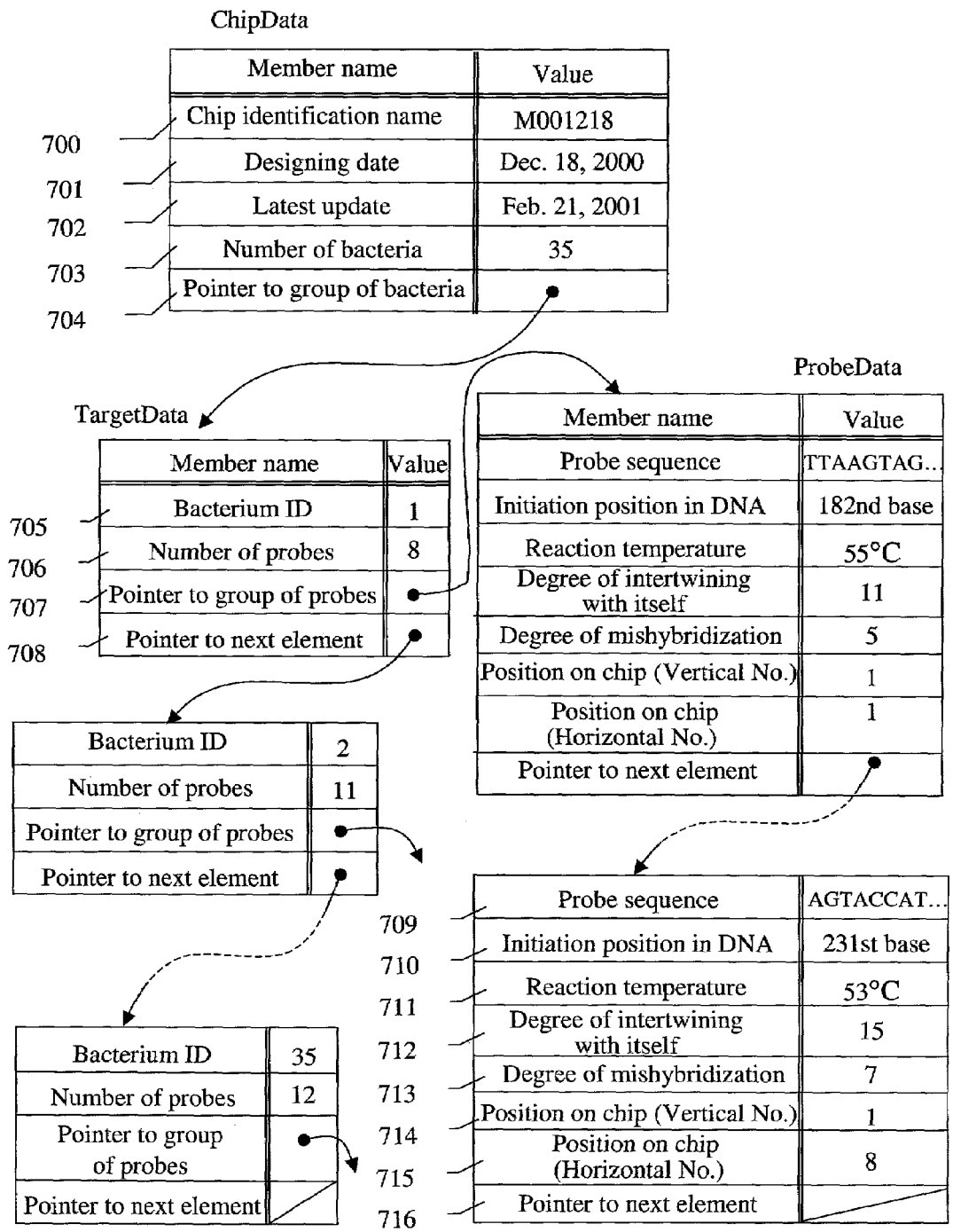
FIG. 7 is a figure showing the structure of DNA chip data.

FIG. 7 is an example of a data structure of a DNA chip that is read from the DNA chip database 401 and retained in the DNA chip data 417 in the data memory 415. In the present system, this data structure is used for design and updation of probes of a DNA chip.

700 denotes the identification name of the DNA chip. This identification name is displayed in the chip identification name 500 in the probe selection result display screen in FIG. 5. 701 and 702 denote the designing date and the latest update date of the DNA chip, respectively. These are displayed in 501 and 502 in the probe selection result display screen. 703 denotes the number of bacteria that are defined as identification objects. This is displayed in 503 in the probe selection result display screen. 704 denotes a group of bacteria that are defined as identification objects. The data of a TargetData structure that is shown next is retained as a list structure, and a pointer pointing to the next leading element is stored herein. The number of elements in the list is same as the value in 703.

705 to 708 represent the data of the TargetData structure. 705 is the ID number of a bacterium. 706 is the number of probes selected to identify this bacterium. 707 is a group of probes selected to identify this bacteria. The data of a ProbeData structure that is shown next is retained as a list structure, and a pointer pointing to the next leading element is stored herein. The number of elements in the list is same as the value in 706. 708 is a pointer pointing to the next TargetData structure. Where it is the last bacterium, the pointer becomes a null pointer.

709 to 716 represent the data of the ProbeData structure. 709 is the DNA sequence of a probe. This information is displayed in the probe selection result display screen 505. 710 is an initiation position of the probe in DNA and shows at which base the probe is placed, when counting from the beginning of the DNA sequence of a bacterium. This information is displayed in 505 of the probe selection result display screen. 711 denotes hybridization temperature of the probe. This information is displayed in 505 of the probe selection result display screen. 712 denotes a degree of the probe intertwining with itself. This information may be displayed in 505 of the probe selection result display screen. 713 denotes a degree of the probe mishybridizing with other bacteria. This information may be displayed in 505 of the probe selection result display screen. 714 and 715 denote the position of the probe on a DNA chip. 714 and 715 retain the values of a vertical number and a horizontal number, respectively. 716 is a pointer pointing to the next ProbeData structure. Where it is the last probe, the pointer becomes a null pointer.

Figure 8:
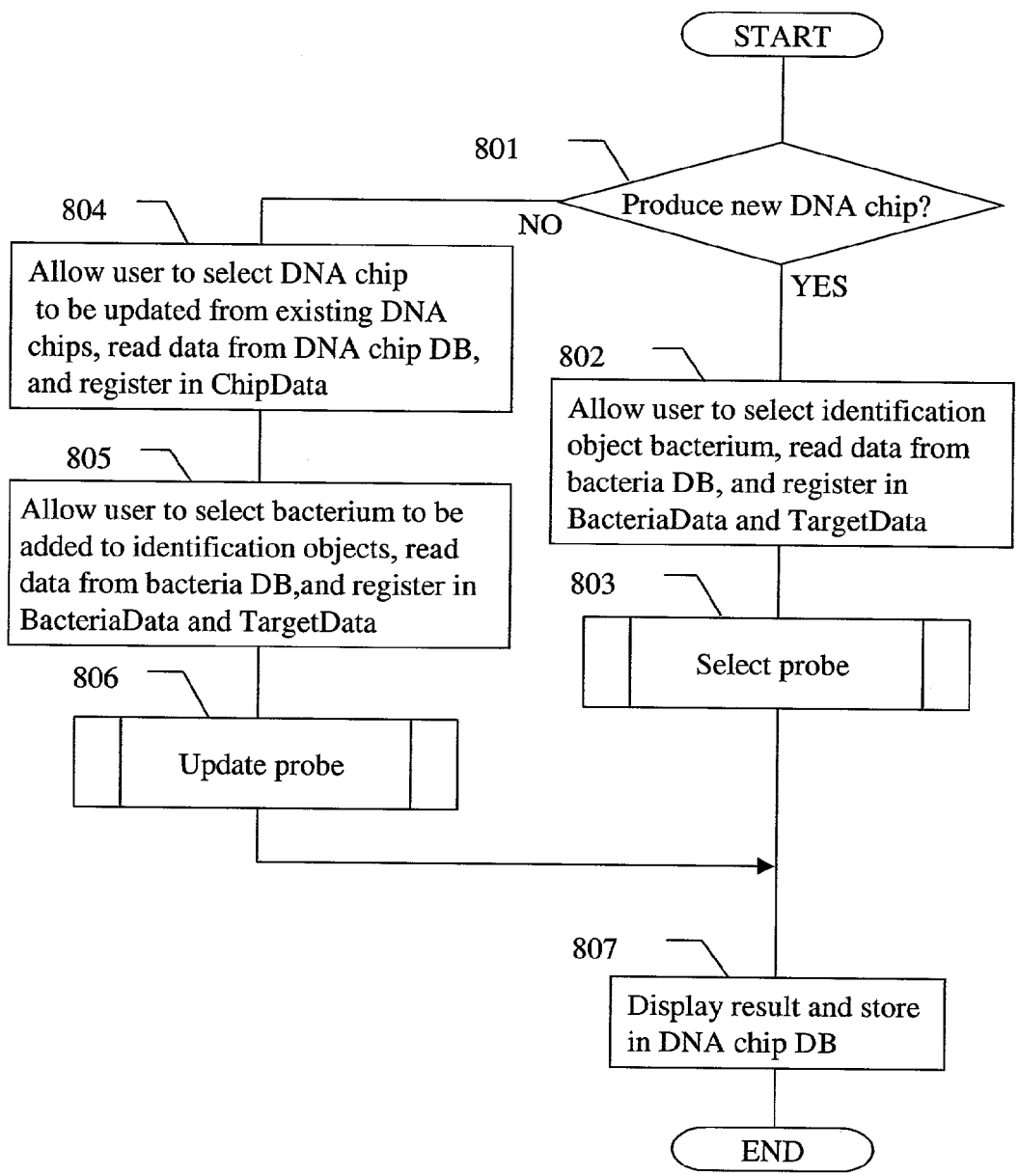
FIG. 8 is a figure showing the general processing flow of the present invention.

FIG. 8 is the general processing flow of the present invention. The processing will be explained below, in accordance with the flow.

First, the user is allowed to select whether the user designs a new probe on a DNA chip or updates probe information on the existing DNA chip, using the keyboard 403, the mouse 404, etc. (Step 801). In step 801, where a DNA chip is newly designed, a process by the identification object bacterium registration processing unit 407 is carried out. That is, the user is allowed to input a group of identification object bacteria, using the keyboard 403, the mouse 404, etc., and then the corresponding data is read from the bacteria database 400 (Step 802). The structure of data that is read herein is BacteriaData shown in FIG. 6. The screen image herein is as shown in FIG. 24. The selected bacteria information is registered in the bacteria data 416 and TargetData of the DNA chip data 417 in a data memory, and connected by the pointer 708 pointing to the next element in a list structure. Then, a process by the probe new selection processing unit 409 is carried out. That is, based on these data, probes on a DNA chip are selected (Step 803). The details of the probe selection process will be explained later.

In the step 801, where probe information on the existing DNA chip is updated, first, the user is allowed to select a DNA chip that is an updation object, using the keyboard 403, the mouse 404, etc., and then the corresponding data is read from the DNA chip database 401 and registered in the DNA chipdata 417 in the data memory (Step 804). The structure of data that is read herein is ChipData shown in FIG. 7. Moreover, the data of bacteria that are identification objects of the selected DNA chip are read from the bacteria database 400. The structure of data that is read herein is BacteriaData shown in FIG. 6. Thereafter, a process by the identification object bacterium addition processing unit 408 is carried out. That is, the user is allowed to select a bacterium to be newly added to identification objects, using the keyboard 403, the mouse 404, etc., and then the corresponding data is read from the bacteria database 400 (Step 805). The structure of data that is read herein is as shown in FIG. 6. The screen image herein is as shown in FIG. 25. The selected bacteria information is registered in the bacteria data 416 and TargetData of the DNA chip data 417 in the data memory, and the list structure is extended by the pointer 708 pointing to the next element. Then, a process by the probe updation processing unit 410 is carried out. That is, based on these data, probe information on the DNA chip is updated (Step 806). The details of the probe information update process will be explained later.

Finally, a process by the probe information display processing unit 414 is carried out. That is to say, selection results are displayed and stored in the DNA chip database 401 (Step 807). The screen image herein is as shown in FIG. 5.

Figure 9:
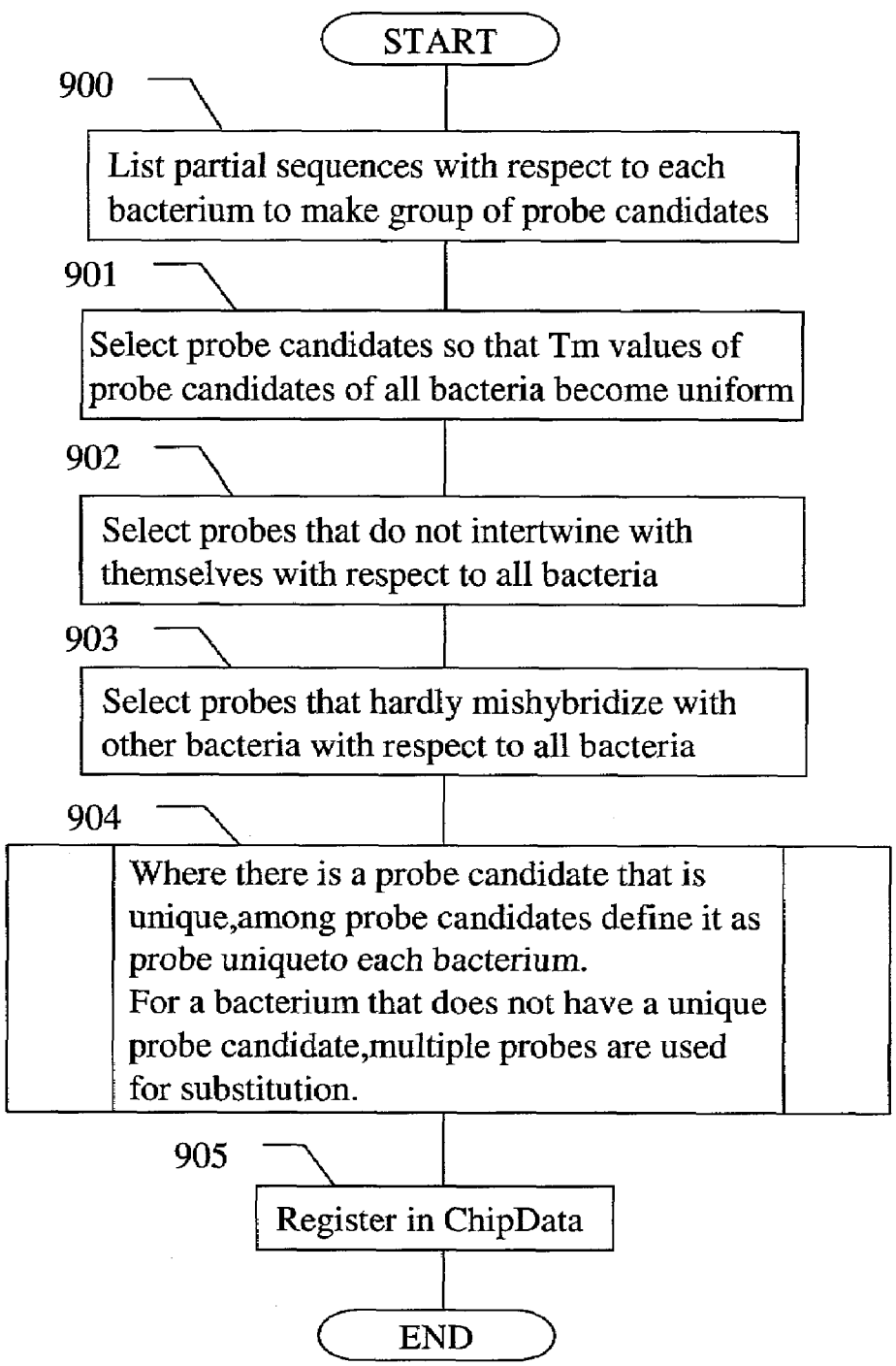
FIG. 9 is a figure showing the detailed flow of a process of selecting probes.

FIG. 9 shows a process by the probe new selection processing unit 409, that is, the detailed flow of a process of newly selecting probes on a DNA chip (Step 803) in FIG. 8. The processing will be explained below, in accordance with the flow.

First, partial sequences are listed for each bacterium to make a group of probe candidates (Step 900). As shown in FIG. 10, all partial sequences contained in the DNA sequence of a bacterium are defined as probe candidates, and then probe candidates satisfying the conditions such as Tm value, a degree of intertwining with itself and a degree of mishybridization, are selected therefrom (Steps 901 to 903), such as DNA sequences R (SEQ ID NO. 7). In FIG. 10, the length of all probes is the same, but probes having various lengths may also be designed. In that case, the partial sequence of each length is listed.

Probe candidates are selected so that Tm value of all the probe candidates becomes the same (Step 901). Tm value means a temperature at which DNA's double strands become a single strand (and vice versa), and the value is determined by the ratio (GC content) of G (guanine) and C (cytosine) contained in a DNA sequence. Since all probes on a DNA chip are subjected to an experiment at the same temperature, it is desired that all the probes have the same Tm value.

FIG. 11 is a figure showing a situation in which probes are selected so as to have the same Tm value. There are three probe candidates (probe candidates 1, 2 and 3) of bacterium P (SEQ ID NO. 8), and the GC content of the probe candidates is 2, 1 and 3, respectively. In addition, there are two probe candidates (probe candidates 1 and 2) of bacterium Q (SEQ ID NO. 9), and the GC content of the probe candidates is 3 and 4, respectively. In this case, where probe candidate 3 of bacterium P and probe candidate 1 of bacterium Q are selected, the GC content becomes 3 and Tm value becomes the same. It is preferred to control the variation of Tm value within the vicinity of 5° C.

Figure 12:
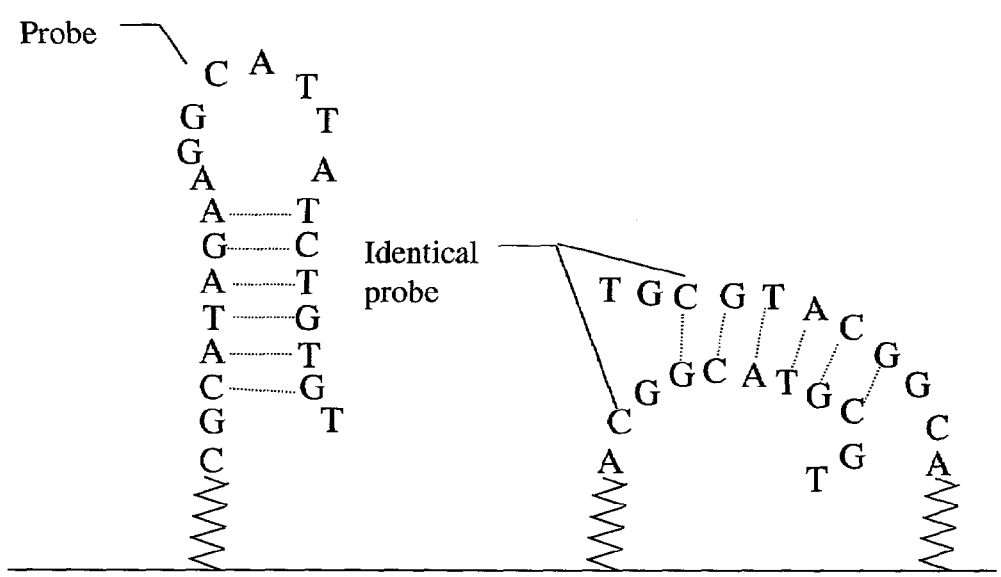
FIG. 12 is a figure showing a state in which a probe intertwines with itself.

For each bacterium, probes that do not intertwine with themselves are selected from the probe candidates (Step 902). As shown in the left example of FIG. 12, if a probe (SEQ ID NO. 10) intertwines with itself, it cannot capture DNA in a sample. As shown in the right example of FIG. 12, if two identical probes (SEQ ID NOs. 11, 12) intertwine with each other, they cannot capture DNA in a sample. Accordingly, to increase sensitivity of detection, it is necessary to select probes that hardly intertwine with themselves. As a criterion of judging intertwinement of probes, it is known to calculate free energy by applying Nearest-Neighbor method to a stacking structure, a bulge loop structure, an internal loop structure, a hairpin structure, a branched loop structure, etc.

Figure 13:
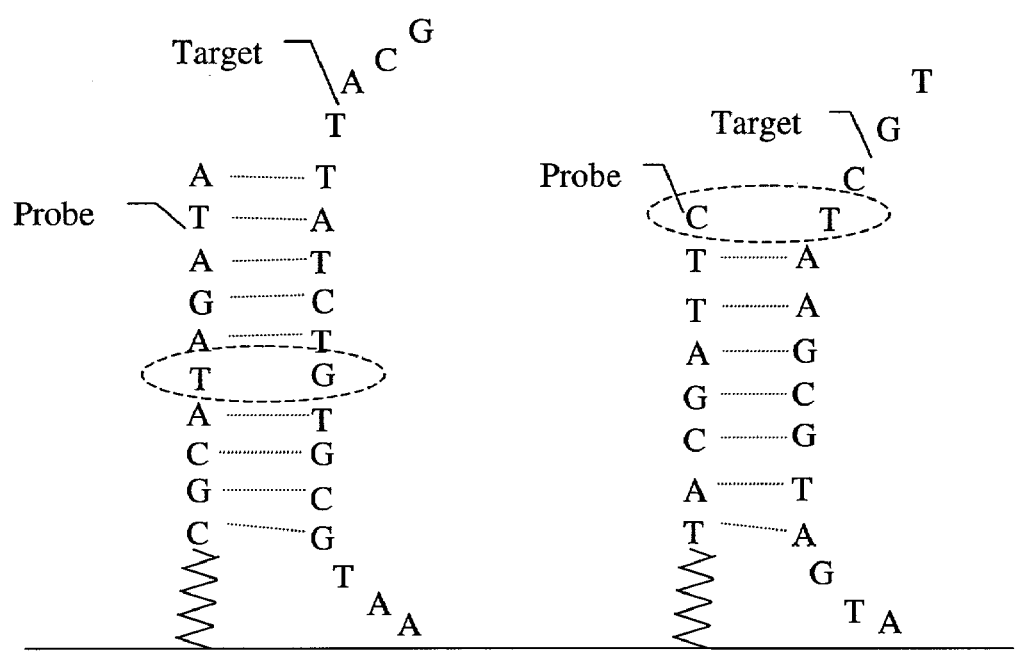
FIG. 13 is a figure showing an example that a probe and DNA in a sample are partially hybridized.

For each bacterium, probes that hardly mishybridize with other bacteria are selected (Step 903). As shown in FIG. 13, where a probe is similar to DNA in a sample, hybridization may occur partially, and it is called mishybridization. In the left example of FIG. 13, there appears a combination of T and G in the middle of a probe (SEQ ID NO. 13) and a target (SEQ ID NO. 14), and in the right example, there appears a combination of C and T at the edge of the probe and another target (SEQ ID NO. 15). Except for these, however, all combinations consist of A and T, and G and C. Thus, once mishybridization occurs, bacteria that do not correspond to probes are misdetected.

For each bacterium, unique probes are selected from the probe candidates. To bacteria which do not have unique probe candidates, the multiple probes substitution processing unit 411 is allowed to operate, and multiple probe candidates are used for substitution. The details of a process of substituting by multiple probes will be explained later (Step 904).

Finally, probe candidates selected in the steps 900 to 904 are defined as probes (Step 905). That is to say, information on a probe corresponding to each bacterium is registered in the members 709 to 715, and it is connected to one another in a list structure, using the pointer 716 pointing to the next element.

The conditions that probes should satisfy were considered above in the order of reaction temperature, a degree of intertwining with itself, a degree of mishybridization with other bacteria and uniqueness, but this order may be changed.

Figure 14:
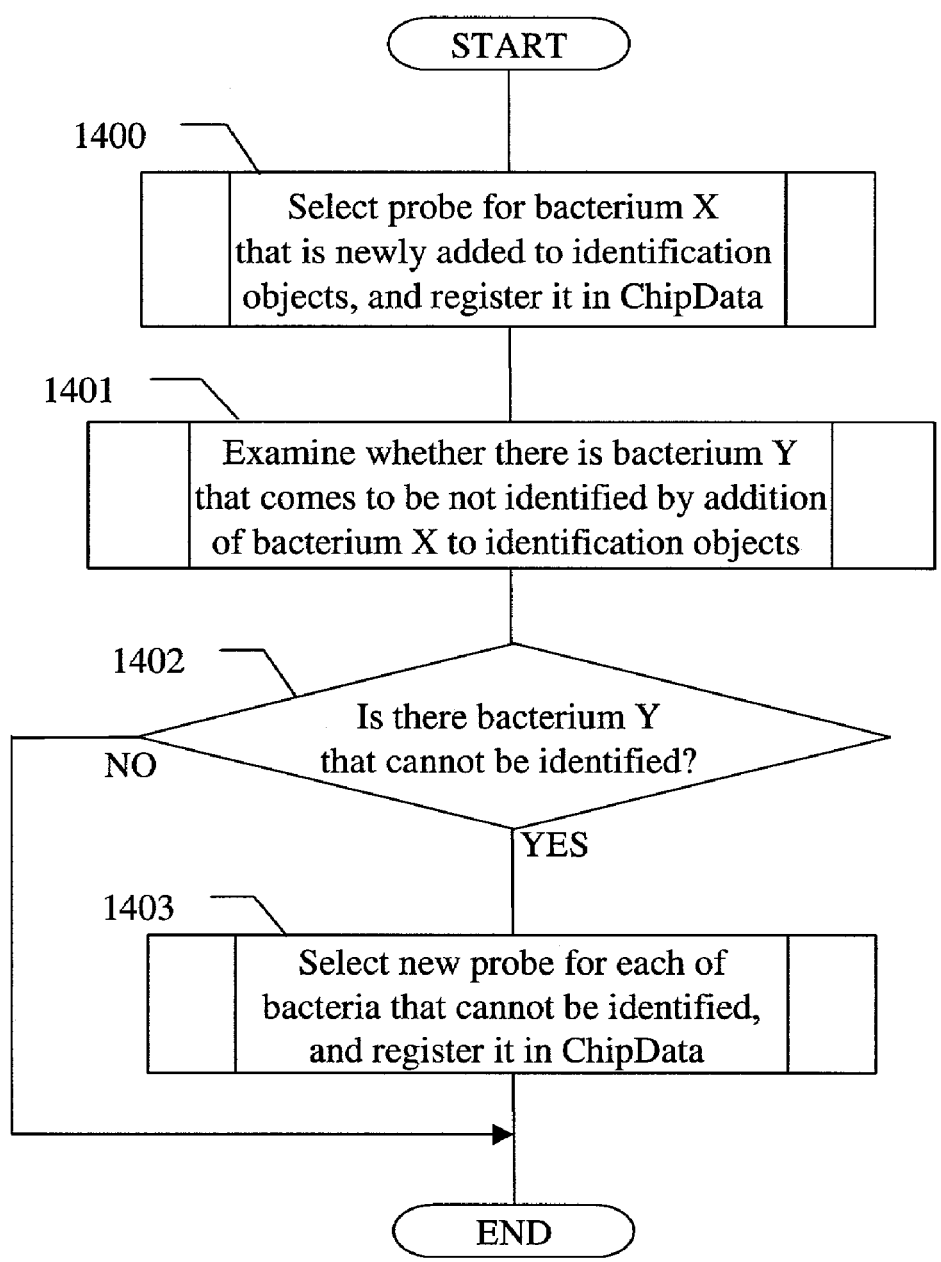
FIG. 14 is a figure showing the detailed flow of a process of updating probes.

FIG. 14 is a figure showing the detailed flow of a process by the probe updation processing unit 410, that is, a process of updating probe information on the existing DNA chip in FIG. 8 (Step 806). The processing will be explained below, in accordance with the flow.

First, a process by the probe addition processing unit 413 is carried out, and probes to be added to identify a newly added bacterium X, are selected and registered in ChipData (Step 1400). A process of selecting probes to be added will be explained in detail later. Next, a process by the probe reanalysis processing unit 412 is carried out to examine whether bacteria that come to be not identified, exist among the previous identification object bacteria (Step 1401). This process also will be explained later. There are some cases where, among the previous identification object bacteria, there exist bacteria that come to be not identified (a bacterium Y), because a bacterium X is added to the identification objects. Where such a bacterium Y exists, a process by the probe addition processing unit 413 is carried out to add probes for identifying the bacterium Y and to update the probe list 704 (Steps 1402 and 1403). Where there are no bacteria that come to be not identified in the step 1402, the process is terminated.

Figure 15:
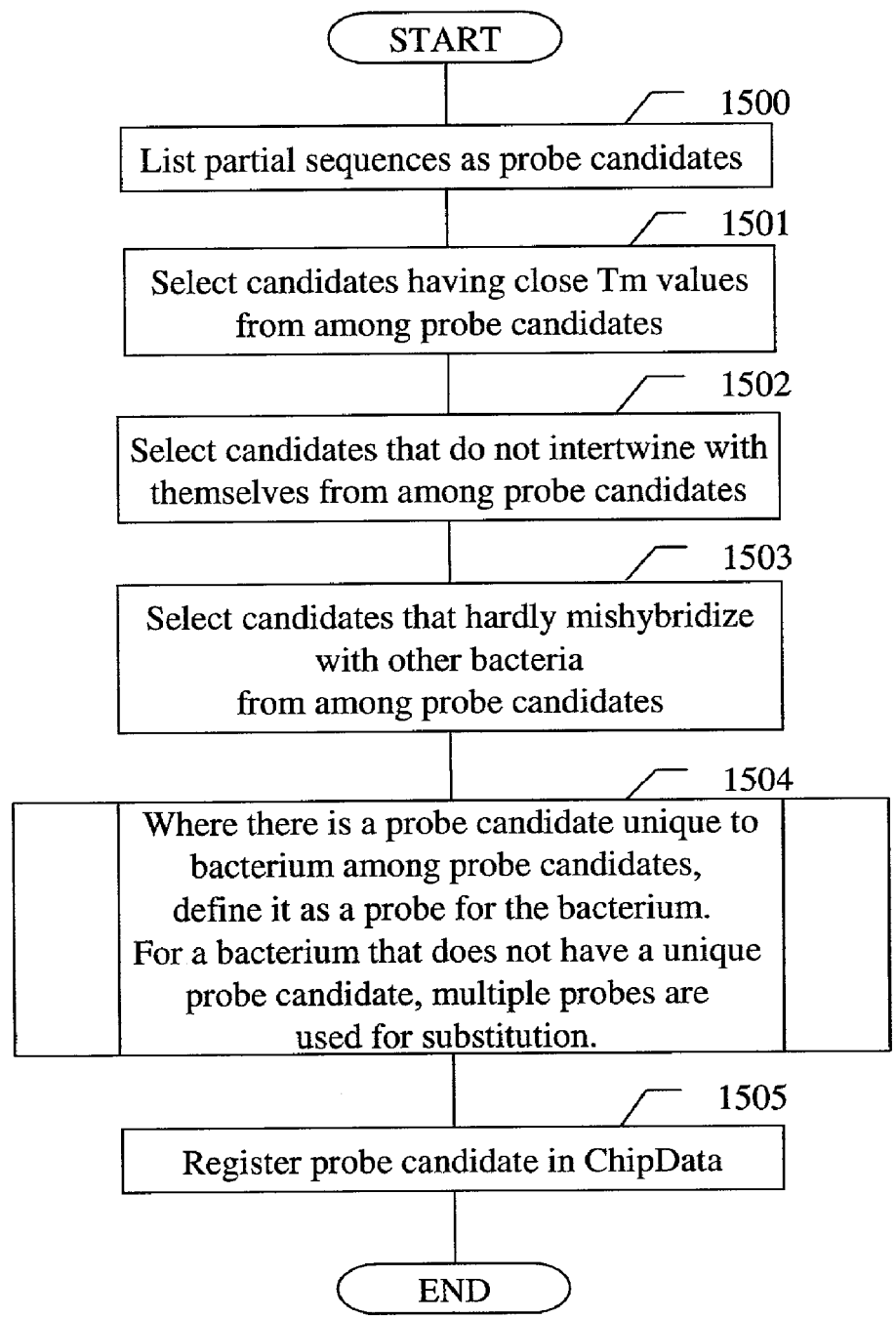
FIG. 15 is a figure showing the detailed flow of a process of adding probes.

FIG. 15 is a figure showing the detailed flow of a process by the probe addition processing unit 413, that is, a process of selecting probes that are added to identify the newly added bacterium X in FIG. 14 (Step 1400). A process of adding probes for identifying the bacterium Y (Step 1403) is the same as that in the step 1400. The processing will be explained below, in accordance with the flow.

First, partial sequences of the bacterium X are listed to make a group of probe candidates (Step 1505). When additional probes are selected for a certain bacterium, for which some probes have already been designed, the existing probes are eliminated from the group of candidates. Next, probes with close Tm values are selected from the probe candidates (Step 1501).

Figure 16:
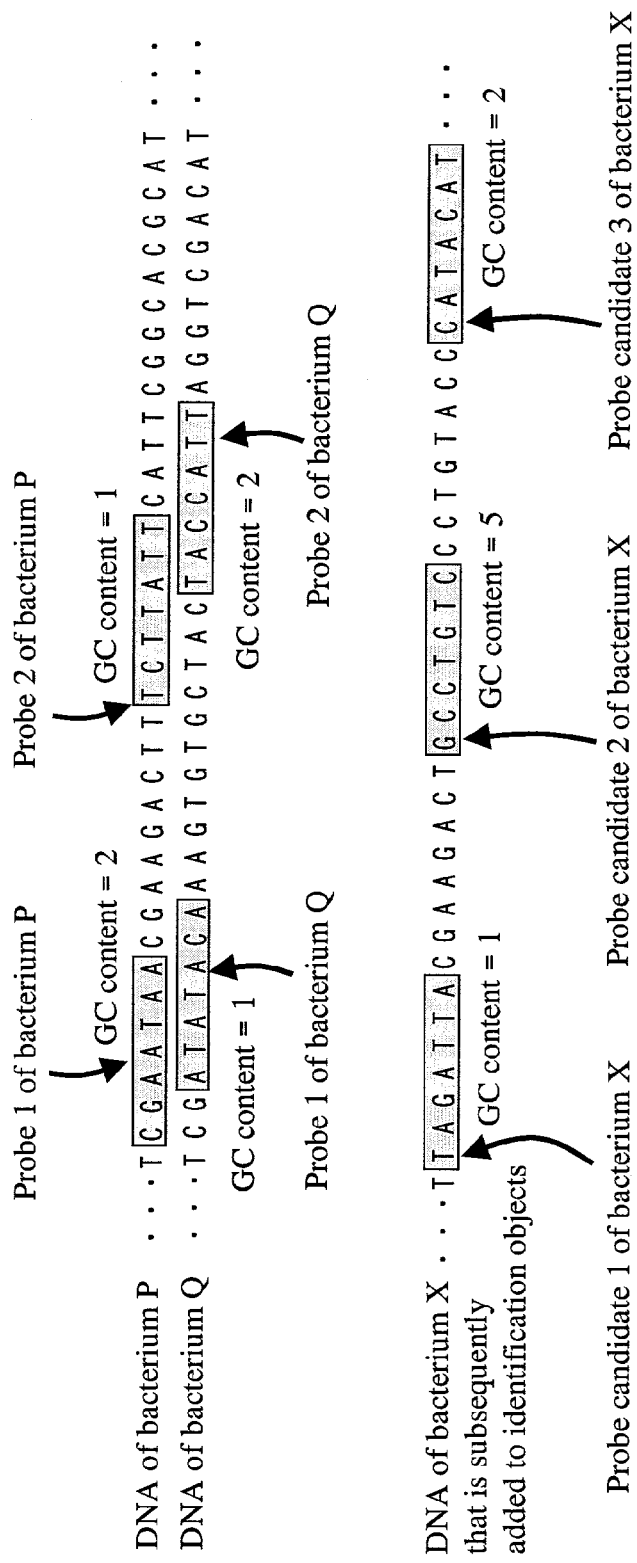
FIG. 16 is a figure showing a process of selecting probes having the same reaction temperature with other probes to the subsequently added identification object bacterium.

FIG. 16 is a figure showing a situation in which probe candidates with close Tm values are selected for the bacterium X (SEQ ID NO. 18) that is newly added to identification objects. It is assumed that a bacterium X is added as a new identification object to a DNA chip that has been designed, having bacteria P (SEQ ID NO. 16) and Q (SEQ ID NO. 17) as identification objects. The GC content of the probes of bacteria P and Q is 1 or 2. Accordingly, in this case, if probes having a GC content within this range (probe candidates 1 and 3 of the bacterium X) are used for the bacterium X, the Tm values of the DNA chip as a whole can be uniformed, so that experimental precision can be increased.

Thereafter, probes that do not intertwine with themselves are selected from among the probe candidates (Step 1502). This process is the same as that in the step 902.

Candidates having a low probability of mishybridizing with DNA of other bacteria are selected (Step 1503). This process is the same as that in the step 903. Where there are probe candidates unique to the bacterium X, these candidates are defined as probes for the bacterium X (Step 1504). Where there exist no unique probe candidates, multiple probes are used for substitution. The details of a process of substituting by multiple probes will be explained later.

The thus selected probe candidates are defined as probes of the bacterium X and registered in ProbeData. That is to say, probe information is registered in the members 709 to 715, and it is connected to one another in a list structure, using the pointer 716 pointing to the next element (Step 1505).

Herein also, as with FIG. 9, the conditions that probes should satisfy were considered in the order of reaction temperature, a degree of intertwining with itself, a degree of mishybridization, and uniqueness, but this order may be changed.

Figure 17:
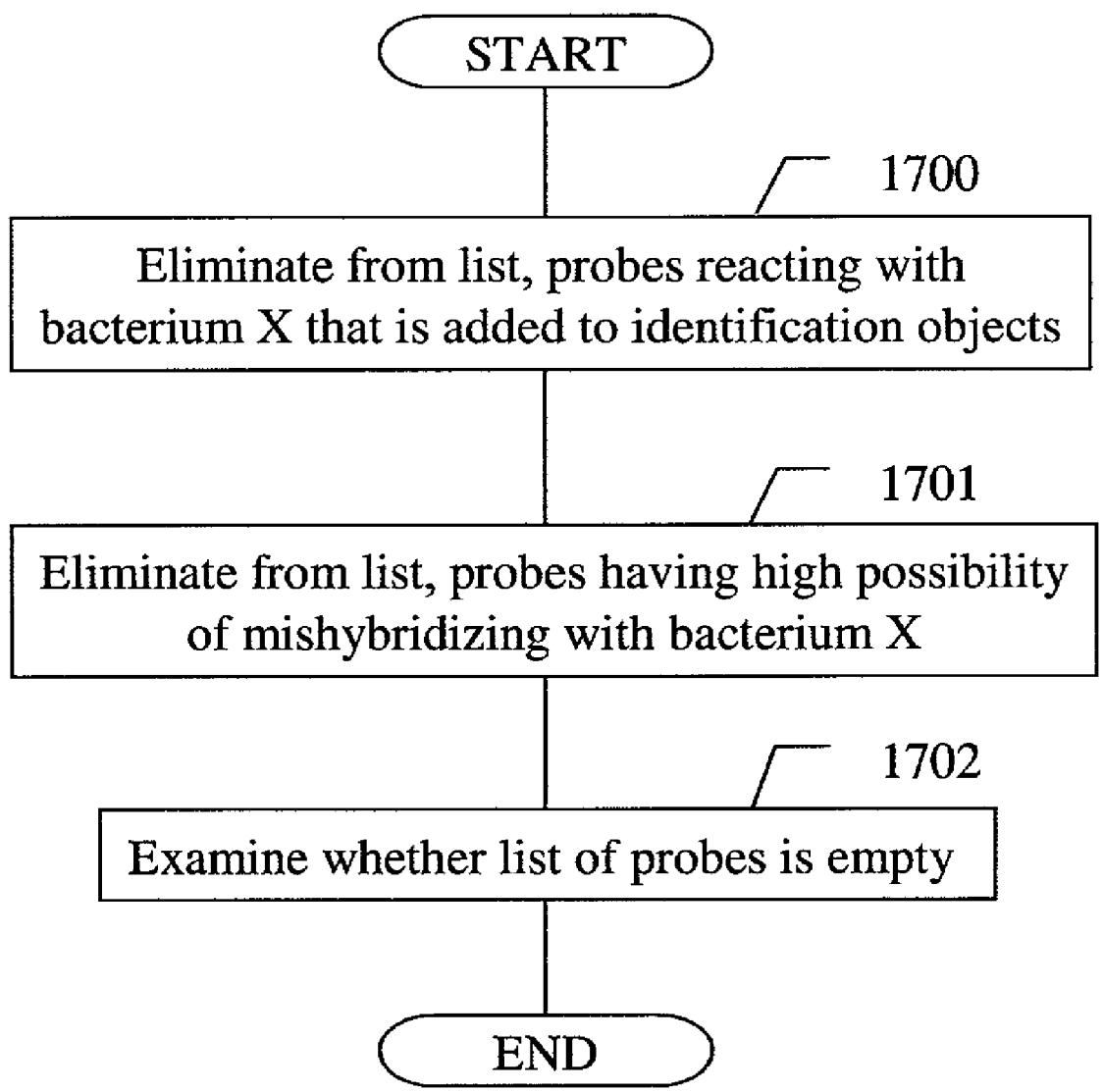
FIG. 17 is a figure showing the detailed flow of a process of examining whether or not an unidentified bacterium exists.

FIG. 17 is a figure showing the detailed flow of a process by the probe reanalysis processing unit 412, that is, a process of examining whether there exist bacteria that cannot be identified in FIG. 14 (Step 1401). The process shown in the flow is carried out on each bacterium. The processing will be explained below, in accordance with the flow.

Figure 18:
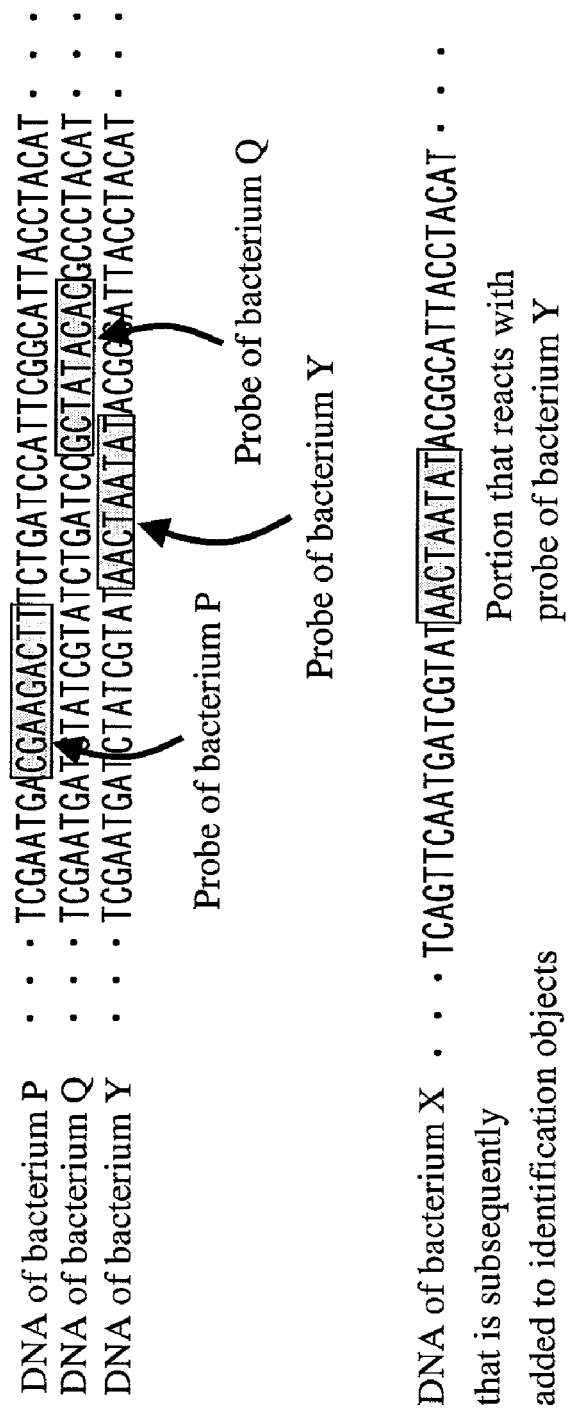
FIG. 18 is a figure showing a state in which a probe loses uniqueness by subsequent addition of an identification object bacterium.

First, among probes of the bacterium Y, probes that also react with the bacterium X are eliminated from the list 707 (Step 1700). This is because, in some cases, the DNA sequence of a bacterium that is subsequently added, comprises the sequence of a probe as a partial sequence. FIG. 18 shows a situation in which a bacterium X (SEQ ID NO. 22) is newly added as an identification object, after probes have been designed for bacteria P (SEQ ID NO. 19), Q (SEQ ID NO. 20) and Y (SEQ ID NO. 21) as identification objects. Since the DNA sequence of the bacterium X comprises probes of the bacterium Y as partial sequences, the probes of the bacterium Y react with both of the bacteria X and Y. Thus, because of addition of the bacterium X, the presence of the bacterium Y cannot properly be determined by using the probes of the bacterium Y.

Then, among probes of the bacterium Y, the probes that mishybridize with the bacterium X are eliminated from the list 707 (Step 1701). That is because, in some cases, the bacterium X that is newly added as an identification object, mishybridize with probes of the bacterium Y with high probability. FIG. 19 shows a situation in which a bacterium X is newly added as an identification object, after probes have been designed for bacteria P, Q and Y as identification objects. Since probes of the bacterium Y have a low similarity to the DNA sequences of the bacteria P and Q, there was a low possibility of mishybridization before the bacterium X is added. However, since the DNA sequence of the bacterium X has a high similarity to probes of the bacterium Y, there is a high possibility to incorrectly determine the bacteria Y and X. Thus, by addition of the bacterium X, probes of the bacterium Y lose optimality.

It is examined whether the probe list has become empty as a result of eliminating probes in the steps 1700 and 1701 (Step 1702). If the list is empty, it is impossible to distinguish the bacterium Y from the bacterium X that is added to identification objects. So, as explained in the step 1403, it is necessary to add probes. If the list is not empty, the bacterium Y can be identified with the remaining probes, and so there is no need for addition of probes.

Figure 21:
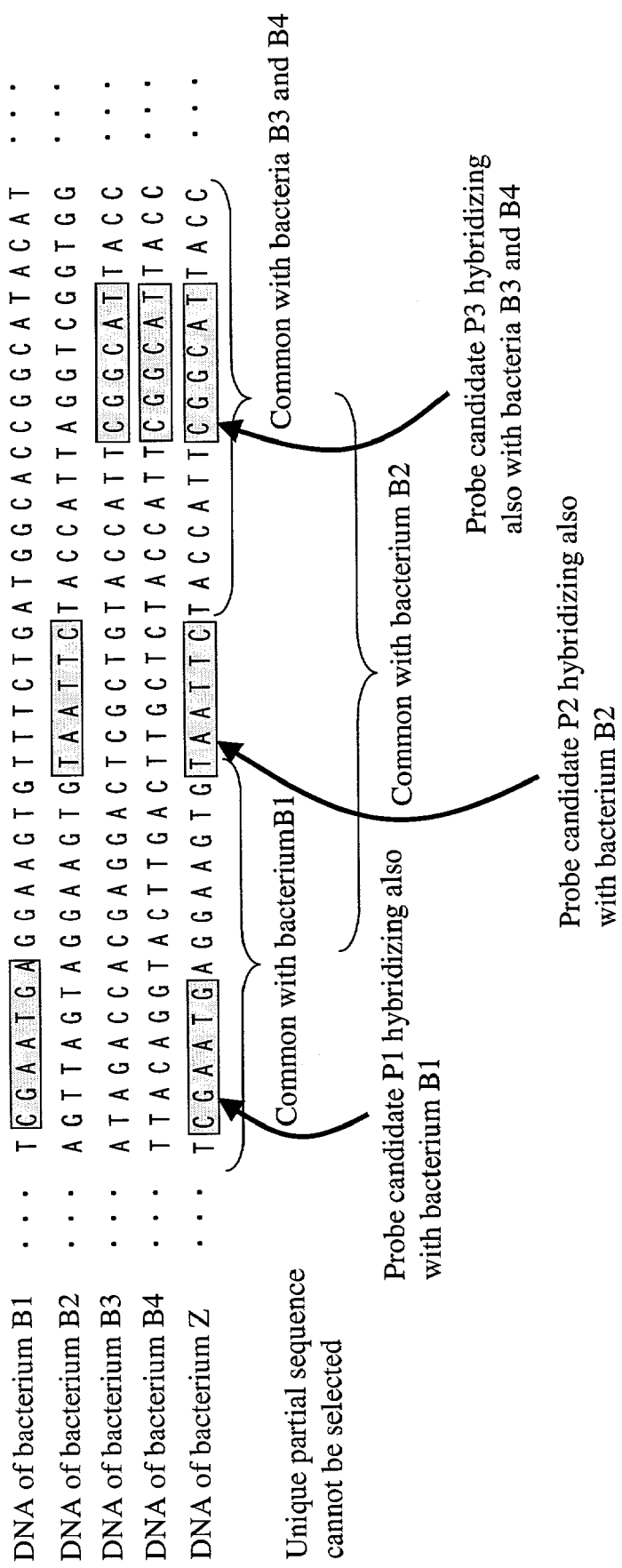
FIG. 21 is a figure showing selection of multiple probe candidates, where a probe unique to the DNA of an identification object bacterium cannot be designed.

FIG. 20 is a figure showing the detailed flow of a process by the multiple probes substitution processing unit 411, that is, a process of substituting by multiple probes when probes unique to the identification object bacterium Z in FIGS. 9 and 15 cannot be designed (Steps 904 and 1504). FIG. 21 is a figure showing a state in which unique partial sequences cannot be selected since the DNA sequence of the bacterium Z (SEQ ID NO. 27) is common to those of bacteria B1 (SEQ ID NO. 23), B2 (SEQ ID NO. 24), B3 (SEQ ID NO. 25) and B4 (SEQ ID NO. 26). For the sake of simplicity, assuming that probes unique to each of bacteria B1, B2, B3 and B4 can be designed, the processing will be explained below.

First, all the partial sequences of the bacterium Z are listed as probe candidates (Step 2000). In FIG. 21, for the sake of simplicity of explanation, only three probes, P1, P2 and P3, are defined as probe candidates, but in reality, all the partial sequences of the bacterium Z are defined as probe candidates. Then, regarding each of the probe candidates, it is examined how many candidates react with bacteria other than the bacterium Z (Step 2001). In FIG. 21, the probe candidate P1 hybridizes also with the bacterium B1, the probe candidate P2 hybridizes also with the bacterium B2, and the probe candidate P3 hybridizes also with the bacteria B3 and B4.

Subsequently, a probability of correctly identifying is enhanced by the following two schemes (Step 2002). The first scheme is use of multiple probes. First, a case where P1 is used as a probe of the bacterium Z is considered. As shown in FIG. 22, when the bacterium B1 is present, a signal is observed from P1, regardless of the presence or absence of the bacterium Z. Consequently, when the bacterium B1 is present (regardless of the presence of the bacterium B2), it is impossible to determine whether or not the bacterium Z exists from only the signal of the probe. Then, a case where P1 and P2 are used as probes of the bacterium Z is considered. As shown in FIG. 22, when both the bacteria B1 and B2 are present, signals are observed from both P1 and P2, regardless of the presence of the bacterium Z. Consequently, when both the bacteria B1 and P2 are present, it is impossible to determine whether or not the bacterium Z is present. Since "the probability that both the bacteria B1 and B2 are present" is lower than "the probability that the bacterium B1 is present (the bacterium B2 may or may not be present)", the use of both P1 and P2 can reduce the probability that the presence of the bacterium Z cannot be determined. Where all of the probes, P1, P2 and P3 are used, this probability can further be reduced. However, when the number of probes are increased, cost is also increased.

Hence, probe candidates are narrowed according to the second scheme explained below.

Figure 23:
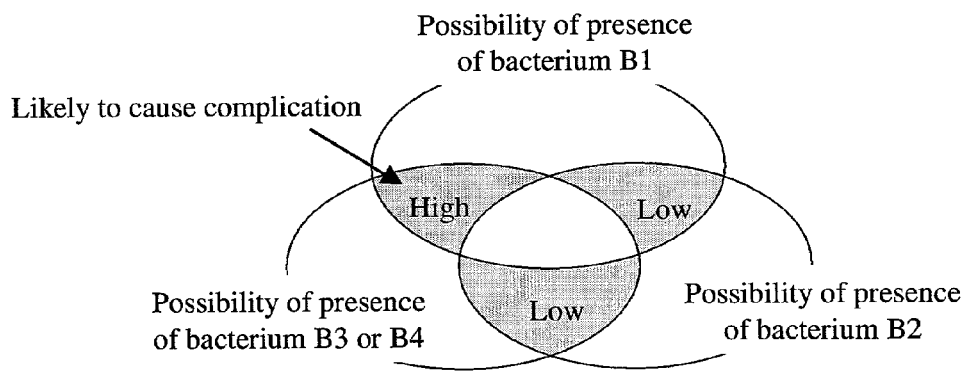
FIG. 23 is a figure showing that a probability of misidentification is changed, depending on how to select probe candidates.

The second scheme is to reduce "the probability that the presence of the bacterium Z cannot be determined", using fewer probes. For example, where two probe candidates are selected, regarding each of combinations "P1 and P2" "P2 and P3" and "P1 and P3", "the probability that the presence of the bacterium Z cannot be determined" is calculated, and a combination of probes having the minimum probability is selected. As shown in FIG. 22, where P1 and P2 are used, it is impossible to determine the presence of the bacterium Z if both the bacteria B1 and B2 are present. As shown in FIG. 23, regarding combinations, "P2 and P3" and "P1 and P3" also, cases where it is impossible to make the determination, are obtained. Then, there are considered "a possibility of both the bacteria B1 and B2 simultaneously existing in a sample", "a possibility that the bacterium B2 is present, and bacterium B3 or B4 are present" and "a possibility that the bacterium B1 is present, and bacterium B3 or B4 is present". As shown in the following examples, bacteria contributing to a complication or mixed infection are known.

Example 1

Influenza is likely to contribute to a complication with bacterial pneumonia (Kakogawa-shi, Kako-gun, Medical Association Infectious Disease Information Provision System, Memo. 20, dated 98.2.1)

Example 2

MRSA (methicillia resistant *staphiococcus aureus*) simultaneously exists with *Pseudomonas aeruginosa* with high probability (Homepage of Inasa Redcross Hospital, updated 1996/07/26)

Example 3

Vancomycin resistant Enterococcus is likely to contribute to a mixed infection with *Pseudomonas aeruginosa* or *Escherichia coli* (Infectious Diseases Weekly Report: Story about Infectious Diseases, 2000, the 20th week (May 15 to May 21), the 21st week (May 22 to May 28)

Example 4

*Chiamydial pneumonia* often contributes to a mixed infection with *Mycoplasma pneumomae* or *Diplococcus pneumoniae* (Infectious Diseases Weekly Report: Story about Infectious Diseases, 1999, the 45th week (November 8 to November 14)

Example 5

*Giardia lamblia* disease contributes to a mixed infection with *Shigella dysenteriae*, enteropathogenic *Escherichia coli* or *Entamoeba dysenteriae* (Infectious Diseases Weekly Report: Story about Infectious Diseases, 2000, the 12th week (March 20 to March 26)

Example 6

*Entamoeba dysenteriae* infectious disease may contribute to a complication with other venereal diseases (e.g. syphilis, HIV, hepatitis B, herpes progenitalis, etc.) (Infectious Diseases Weekly Report: Story about Infectious Diseases, 2000, the 29th week (July 17 to July 23)

Example 7

Acquired immune deficiency syndrome (AIDS) contributes to a complication with *Pneumocystis carinii* pneumonia, oral candidiasis, toxoplasmosis, herpes zoster, atypical mycobacteriosis, *Entamoeba dysenteriae*, an antifungal agent or a cytomegalovirus infection (Infectious Diseases Weekly Report: Story about Infectious Diseases, 2000, the 23rd week (June 5 to June 11)

Example 8

Gram-negative bacillus contributes to a mixed infection with *Candida* (Hirohito Ishikawa et al., "Candidemia causing decrease of cellular immunity against malignancy after gastrectomy" The 98th Annual Congress of Japan Surgical Society, Topic No. P-114 ; Hideyo Yamaguchi, "Problems on fungus infections", The 24th Annual Congress of Japan Burn Society, Scientific Congress, Educational Lecture).

Example 9

*Bacillus diphtheriae* contributes to a mixed infection with chain coccus or staphylococcus (Manual for preventing diphtheria, National Institute of Infectious Diseases, Bacteria/Blood Product Division, Department of Microbiology Reference Committee, Diphtheria Sub-Committee).

Example 10

*Salmonella Typhi* contributes to a mixed infection with *Salmonella* or *Giardia lamblia* (Infectious Agents Surveillance Report Vol. 17, No. 12: IASR)

There is a high possibility that the combinations of bacteria that are likely to contribute to a complication as stated above, simultaneously exist in a sample. FIG. 23 shows that since it is very likely that bacterium B1 and bacterium B3 or B4 cause a complication and exist simultaneously, a combination of probe candidates, "P1 and P3", has a higher probability ="that the presence of bacterium Z that cannot be determined"= than combinations "P1 and P2" and "P2 and P3". Such information on a complication and a mixed infection is obtained from the data 605 of the bacteria database 400, and combinations of probe candidates are selected so as to reduce "a probability that the presence of bacterium Z cannot be determined".

In the above explanation, identification of bacteria was taken as an example, but identification of other organisms or DNA that are mixed in a sample is also carried out in the same manner. Moreover, only the complication and the mixed infection of bacteria were pointed out as materials for evaluation of a possibility of simultaneous existence of multiple types of identification object DNA in a sample, but the evaluation can also be made by medical or biological knowledge regarding whether growth conditions are identical, or whether the identification objects are in predator-prey relation, competitive relationship, symbiotic relationship, etc.

As stated above, according to the present invention, temporal and pecuniary cost to produce a DNA chip ready for a new bacterium can be reduced. Even where a unique probe cannot be designed, a DNA chip capable of identifying with high probability can be produced.

What is claimed is:

1. A method of designing a biochip for identifying multiple kinds of targets via hybridization, comprising:

a step of reading data of base sequences of the targets;

for each of the targets, a step of (1) selecting one of partial sequences of a base sequence of a respective one of the targets, if said respective target has a partial sequence unique with respect to base sequences of other targets, or (2) selecting partial sequences of the base sequence of said respective one of the targets, as multiple probes, if said respective target does not have a partial sequence unique with respect to base sequences of other targets, each of said multiple probes having a low probability of mishybridization with said other targets;

a step of assigning an ID number to the biochip, and assigning said probe and said multiple probes to be spotted on predetermined positions on the biochip corresponding to said each of the targets respectively; and a step of registering the ID number, said predetermined positions on the biochip, said probe and said multiple probes to be spotted on said predetermined positions on the biochip, and the corresponding targets in a memory.

2. The method according to claim 1, wherein the step of selecting multiple probes involves a step of selecting combinations of multiple probes corresponding to said respective target to increases the probability of specifically identifying the presence of said respective target, while avoiding any combination of probes corresponding to targets causing a mixed infection or a complication.

3. A computer program stored on a computer-readable recording medium for designing a biochip for identifying multiple kinds of targets via hybridization, comprising:

a module for reading data of base sequences of the targets;

a module, for each of the targets, for (1) selecting one of partial sequences of a base sequence of a respective one of the targets, if said respective target has a partial sequence unique with respect to base sequences of other targets, or (2) selecting partial sequences of the base sequence of said respective one of the targets, as multiple probes, if said respective target does not have a partial sequence unique with respect to base sequences of other targets, each of said multiple probes having a low probability of mishybridization with said other targets;

a module for assigning an ID number to the biochip, and assigning said probe and said multiple probes to be spotted on predetermined positions on the biochip corresponding to said each of the targets respectively; and a module for registering the ID number, said predetermined positions on the biochip, said probe and said multiple probes to be spotted on said predetermined positions on the biochip, and the corresponding targets in a memory.

4. A computer-readable recording medium, which records a program for designing a biochip for identifying multiple kinds of targets via hybridization, comprising:

a module for reading data of base sequences of the targets;

a module, for each of the targets, for (1) selecting one of partial sequences of a base sequence of a respective one of the targets, if said respective target has a partial sequence unique with respect to base sequences of other targets, or (2) selecting partial sequences of the base sequence of said respective one of the targets, as multiple probes, if said respective target does not have a partial sequence unique with respect to base sequences of other targets, each of said multiple probes having a low probability of mishybridization with said other targets;

a module for assigning an ID number to the biochip, and assigning said probe and said multiple probes to be spotted on predetermined positions on the biochip corresponding to said each of the targets respectively; and a module for registering the ID number, said predetermined positions on the biochip, said probe and said multiple probes to be spotted on said predetermined positions on the biochip, and the corresponding targets in a memory.

* * * * *

SEQUENCE LISTING

<160> NUMBER OF SEQ ID NOS: 27

<210> SEQ ID NO 1
<211> LENGTH: 43
<212> TYPE: DNA
<213> ORGANISM: Bacterium

<400> SEQUENCE: 1
tcgaatgacg aagactttct gatccattcg gcattaccta cat     43

<210> SEQ ID NO 2
<211> LENGTH: 43
<212> TYPE: DNA
<213> ORGANISM: Bacterium

<400> SEQUENCE: 2
tcgaatgatc tatcgtatct gatccgctat acacgcccta cat     43

<210> SEQ ID NO 3
<211> LENGTH: 43
<212> TYPE: DNA
<213> ORGANISM: Bacterium

<400> SEQUENCE: 3
tcgaatgatc tatcgtataa ctaatatacg gcattaccta cat     43

<210> SEQ ID NO 4
<211> LENGTH: 31
<212> TYPE: DNA
<213> ORGANISM: Artificial Sequence
<220> FEATURE:
<223> OTHER INFORMATION: Description of Artificial Sequence: assumed DNA

<400> SEQUENCE: 4
tcgaatgacg aagggttctg atcctgtacc c     31

<210> SEQ ID NO 5
<211> LENGTH: 31
<212> TYPE: DNA
<213> ORGANISM: Artificial Sequence
<220> FEATURE:
<223> OTHER INFORMATION: Description of Artificial Sequence: assumed DNA

<400> SEQUENCE: 5
tctgatccat tcgggttctt ctaccattag g     31

<210> SEQ ID NO 6
<211> LENGTH: 31
<212> TYPE: DNA
<213> ORGANISM: Artificial Sequence
<220> FEATURE:
<223> OTHER INFORMATION: Description of Artificial Sequence: assumed DNA

<400> SEQUENCE: 6
tctgatccat tcgggttctg atcctgtacc c     31

<210> SEQ ID NO 7
<211> LENGTH: 31
<212> TYPE: DNA
<213> ORGANISM: Artificial Sequence
<220> FEATURE:
<223> OTHER INFORMATION: Description of Artificial Sequence: assumed DNA

<400> SEQUENCE: 7

```
atagaccacg aggactcgct gtaccattcg g                           31

<210> SEQ ID NO 8
<211> LENGTH: 38
<212> TYPE: DNA
<213> ORGANISM: Bacterium

<400> SEQUENCE: 8
tcgaataacg aagactttct tattcattca ttacgcat                    38

<210> SEQ ID NO 9
<211> LENGTH: 38
<212> TYPE: DNA
<213> ORGANISM: Bacterium

<400> SEQUENCE: 9
tcgaggtaca aagtgtgcta ctaccattag gtcgacat                    38

<210> SEQ ID NO 10
<211> LENGTH: 23
<212> TYPE: DNA
<213> ORGANISM: Artificial Sequence
<220> FEATURE:
<223> OTHER INFORMATION: Description of Artificial Sequence: synthetic
      probe DNA

<400> SEQUENCE: 10
tgtgtctatt acggaagata cgc                                    23

<210> SEQ ID NO 11
<211> LENGTH: 11
<212> TYPE: DNA
<213> ORGANISM: Artificial Sequence
<220> FEATURE:
<223> OTHER INFORMATION: Description of Artificial Sequence: synthetic
      probe DNA

<400> SEQUENCE: 11
tgcgtacggc a                                                 11

<210> SEQ ID NO 12
<211> LENGTH: 11
<212> TYPE: DNA
<213> ORGANISM: Artificial Sequence
<220> FEATURE:
<223> OTHER INFORMATION: Description of Artificial Sequence: synthetic
      probe DNA

<400> SEQUENCE: 12
tgcgtacggc a                                                 11

<210> SEQ ID NO 13
<211> LENGTH: 10
<212> TYPE: DNA
<213> ORGANISM: Artificial Sequence
<220> FEATURE:
<223> OTHER INFORMATION: Description of Artificial Sequence: synthetic
      probe DNA

<400> SEQUENCE: 13
atagatacgc                                                   10

<210> SEQ ID NO 14
<211> LENGTH: 17
<212> TYPE: DNA
```

```
<213> ORGANISM: Bacterium

<400> SEQUENCE: 14
gcattatctg tgcgtaa                                                   17

<210> SEQ ID NO 15
<211> LENGTH: 14
<212> TYPE: DNA
<213> ORGANISM: Bacterium

<400> SEQUENCE: 15
tgctaagcgt agta                                                      14

<210> SEQ ID NO 16
<211> LENGTH: 38
<212> TYPE: DNA
<213> ORGANISM: Bacterium

<400> SEQUENCE: 16
tcgaataacg aagactttct tattcattcg gcacgcat                            38

<210> SEQ ID NO 17
<211> LENGTH: 38
<212> TYPE: DNA
<213> ORGANISM: Bacterium

<400> SEQUENCE: 17
tcgatataca aagtgtgcta ctaccattag gtcgacat                            38

<210> SEQ ID NO 18
<211> LENGTH: 38
<212> TYPE: DNA
<213> ORGANISM: Bacterium

<400> SEQUENCE: 18
ttagattacg aagactgcct gtccctgtac ccatacat                            38

<210> SEQ ID NO 19
<211> LENGTH: 43
<212> TYPE: DNA
<213> ORGANISM: Bacterium

<400> SEQUENCE: 19
tcgaatgacg aagactttct gatccattcg gcattaccta cat                      43

<210> SEQ ID NO 20
<211> LENGTH: 43
<212> TYPE: DNA
<213> ORGANISM: Bacterium

<400> SEQUENCE: 20
tcgaatgatc tatcgtatct gatccgctat acacgcccta cat                      43

<210> SEQ ID NO 21
<211> LENGTH: 43
<212> TYPE: DNA
<213> ORGANISM: Bacterium

<400> SEQUENCE: 21
tcgaatgatc tatcgtataa ctaatatacg gcattaccta cat                      43

<210> SEQ ID NO 22
<211> LENGTH: 43
```

-continued

```
<212> TYPE: DNA
<213> ORGANISM: Bacterium

<400> SEQUENCE: 22
tcagttcaat gatcgtataa ctaatatacg gcattaccta cat         43

<210> SEQ ID NO 23
<211> LENGTH: 38
<212> TYPE: DNA
<213> ORGANISM: Bacterium

<400> SEQUENCE: 23
tcgaatgagg aagtgtttct gatggcaccg gcatacat               38

<210> SEQ ID NO 24
<211> LENGTH: 38
<212> TYPE: DNA
<213> ORGANISM: Bacterium

<400> SEQUENCE: 24
agttagtagg aagtgtaatt ctaccattag gtcggtgg               38

<210> SEQ ID NO 25
<211> LENGTH: 38
<212> TYPE: DNA
<213> ORGANISM: Bacterium

<400> SEQUENCE: 25
atagaccacg aggactcgct gtaccattcg gcattacc               38

<210> SEQ ID NO 26
<211> LENGTH: 38
<212> TYPE: DNA
<213> ORGANISM: Bacterium

<400> SEQUENCE: 26
ttacaggtac ttgacttgct ctaccattcg gcattacc               38

<210> SEQ ID NO 27
<211> LENGTH: 38
<212> TYPE: DNA
<213> ORGANISM: Bacterium

<400> SEQUENCE: 27
tcgaatgagg aagtgtaatt ctaccattcg gcattacc               38
```